US010227571B2

(12) United States Patent
Yoon et al.

(10) Patent No.: US 10,227,571 B2
(45) Date of Patent: Mar. 12, 2019

(54) LACTOBACILLUS PLANTARUM BACTERIOPHAGE LAC-PLP-1 AND USE THEREOF FOR INHIBITING LACTOBACILLUS PLANTARUM PROLIFERATION

(71) Applicant: Intron Biotechnology, Inc., Gyeonggi-do (KR)

(72) Inventors: Seong Jun Yoon, Seoul (KR); Sang Hyeon Kang, Seoul (KR); Soo Youn Jun, Seoul (KR); Jee Soo Son, Seoul (KR); Hyoun Rok Paik, Incheon (KR); Hee Jeong Shin, Gyeonggi-do (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 0 days.

(21) Appl. No.: 15/543,723

(22) PCT Filed: Jan. 5, 2016

(86) PCT No.: PCT/KR2016/000030
§ 371 (c)(1),
(2) Date: Jul. 14, 2017

(87) PCT Pub. No.: WO2016/122128
PCT Pub. Date: Aug. 4, 2016

(65) Prior Publication Data
US 2018/0119109 A1 May 3, 2018

(30) Foreign Application Priority Data
Jan. 29, 2015 (KR) .................. 10-2015-0014188

(51) Int. Cl.
*A61K 48/00* (2006.01)
*C12N 7/00* (2006.01)
*C12P 7/06* (2006.01)
*C12R 1/25* (2006.01)

(52) U.S. Cl.
CPC .................. *C12N 7/00* (2013.01); *C12P 7/06* (2013.01); *C12N 2795/10321* (2013.01); *C12R 1/25* (2013.01)

(58) Field of Classification Search
CPC ...................................................... C12N 7/00
See application file for complete search history.

(56) References Cited

U.S. PATENT DOCUMENTS

| 2009/0104157 A1 | 4/2009 | Solomon et al. |
| 2014/0273137 A1 | 9/2014 | Donovan et al. |

FOREIGN PATENT DOCUMENTS

| KR | 10-2015-0013453 | 1/2015 |
| KR | 10-2015-0014188 | 1/2015 |
| WO | PCT/KR2016/000029 | 1/2016 |
| WO | PCT/KR2016/000030 | 1/2016 |
| WO | WO-2016/122127 A1 | 8/2016 |
| WO | WO-2016/122128 A1 | 8/2016 |

OTHER PUBLICATIONS

Marco et al (International Dairy Journal vol. 39 pp. 64-70) (Year: 2014).*
Marco et al (Applied and Environmental Microbiology vol. 78 (24) pp. 8719-8734) (Year: 2012).*
Lu, Z. et al. (2003) Isolation and Characterization of a *Lactobacillus plantarum* Bacteriophage, ΦJL-1, from a Cucumber Fermentation. Int J Food Microbiol. 84(2):225-35.
Marco, M.B. et al. (2012) Characterization of Two Virulent Phages of *Lactobacillus plantarum*. Appl Environ Microbiol. 78(24):8719-34.
NCBI, *Lactobacillus* phage ATCC 8014-B2, complete Genome. GenBank Accession No. JX486088.1 (Nov. 20, 2012).
Roach, D.R. et al. (2013) Bacteriophage-encoded Lytic Enzymes Control Growth of Contaminating *Lactobacillus* Found in Fuel Ethanol Fermentations. Biotechnol Biofuels. 6:20 (inner pp. 1-11).
Silva, J.B. et al. (2014) Bacteriophages as Antimicrobial Agents Against Bacterial Contaminants in Yeast Fermentation Processes. Biotechnol Biofuels. 7:123 (inner pp. 1-11; See abstract, pp. 3-8).
International Search Report dated Apr. 25, 2016 by the International Searching Authority for International Patent Application No. PCT/KR2016/000030, which was filed on Jan. 5, 2016 and published as WO 2016/122128 on Aug. 4, 2016 (Inventor—Yoon et al.; Applicant—Intron Biotechnology, Inc.) (Original—5 pages/Translation—3 pages).
U.S. Appl. No. 15/543,634 (2017/369852), filed Jul. 14, 2017 (Dec. 28, 2017), Seong Jun Yoon (Intron Biotechnol., Inc.).
Fukao, M. et al., Genomic Analysis by Deep Sequencing of the Probiotic *Lactobacillus brevis* KB290 Harboring Nine Plasmids Reveals Genomic Stability. PLoS ONE. 2013; 8(3): e60521 (10 pages).
Kelly, D. et al., Isolation and Characterization of Bacteriophages the Inhibit Strains of *Pediococcus damnosus*, *Lactobacillus brevis*, and *Lactobacillus paraplantarum* that Cause Beer Spoilage. J Amer Soc Brewing Chemists. 2011; 69(1):8-12 (See abstract, pp. 9-12).
Lu, Z. et al., Bacteriophage Ecology in a Commercial Cucumber Fermentation. Appl Environ Microbiol. 2012; 78(24):8571-8.
Mahony, J. et al., Phages of Lactic Acid Bacteria: The Role of Genectics in Understanding Phage-Host Interactions and Their Co-Evolutionary Process. Virology. 2012; 434:143-50.

(Continued)

*Primary Examiner* — Albert M Navarro
(74) *Attorney, Agent, or Firm* — Ballard Spahr LLP

(57) ABSTRACT

The present invention relates to a Siphoviridae bacteriophage Lac-PLP-1 that is isolated from the nature and can kill *Lactobacillus plantarum* cells specifically, which has a genome represented by the nucleotide sequence of SEQ. ID. NO: 1 (Accession NO: KCTC 12665BP), and a method for preventing and treating the contaminations of *Lactobacillus plantarum* by using the composition comprising the bacteriophage as an active ingredient.

2 Claims, 2 Drawing Sheets
Specification includes a Sequence Listing.

(56) References Cited

OTHER PUBLICATIONS

NCBI, *Lactobacillus brevis* KB290 DNA, Complete Genome. GenBank accession No. AP012167.1 (Mar. 29, 2013) (368 pages).
International Search Report dated Apr. 25, 2016 by the International Searching Authority for International Patent Application No. PCT/KR2016/000029, which was filed on Jan. 5, 2016 and published as WO 2016/122127 on Aug. 4, 2016 (Inventor—Yoon et al.; Applicant—Intron Biotechnology, Inc.) (Original—5 pages/Translation—3 pages).
Non-Final Office Action dated Jun. 14, 2018 by the U.S. Patent and Trademark Office for U.S. Appl. No. 15/543,634, filed Jul. 14, 2017 and published as US 2017/0369852 on Dec. 28, 2017 (Inventor—Yoo et al.; Applicant—Intron Biotechnology, Inc.) (8 pages).

* cited by examiner

SEQUENCE LISTING

<160> NUMBER OF SEQ ID NOS: 1

<210> SEQ ID NO 1
<211> LENGTH: 82025
<212> TYPE: DNA
<213> ORGANISM: Bacteriophage Lac-PLP-1

<400> SEQUENCE: 1

| | | | | | |
|---|---|---|---|---|---|
| gttcatcaca | tgtcgttgtg | tatacaacat | atgttttttc | ttcctcattt | tcgaatgttg | 60 |
| atggtaattc | aacttcatca | tgggcgttat | tgtcaaacga | atctaagtca | atattccatt | 120 |
| tgtttccatc | aaagttaact | ctaattccag | cttcattaag | ctttgaggta | tcaacaactg | 180 |
| gatttttacc | gccagataaa | taatcaataa | cgcttacttc | tttaccatca | tagctacgtt | 240 |
| taaacttcat | ttttacaatc | tccttttaga | atggtaggtc | gtcatcagaa | atatctaatt | 300 |
| gagagccatc | gttggcgaat | gggttagatg | tttcactctt | gttatcatcc | ccaaacccac | 360 |
| tacgagcacc | gctttgagct | ggtgtagagg | cttgaccgtt | agaacgtgag | attgcttctg | 420 |
| tacgttgctt | acgcaattct | tcgtgagcct | tttgaacctg | ttcttcattc | aattctaagt | 480 |
| cactattatc | caatggctta | ccaccagtta | caagtaattg | acgaacatat | gagttagttt | 540 |
| gaacaacttc | gtgaatctga | ccaaatgaac | caccaccgtc | attatcaaca | ttttgcttct | 600 |
| taactactac | atagttcaaa | atattgtagt | acaacatacc | agtgcttcct | tctgggaaga | 660 |
| atccttgcat | gtcaccaatc | aaatcgtcct | taaccttcaa | gtccatgata | cgaccaacac | 720 |
| ggccattgta | gccaacggtt | agtgccttaa | cctatataa | tccagttggg | ttatcttcac | 780 |
| tatccaattc | ttcttcatag | ctttcaataa | ctgccgggat | ttgaccaaat | gcgccatctt | 840 |
| ctaagtcttt | tttatcgttt | acacgatgta | aggtggttgc | tcggaagcga | tttgattcgt | 900 |
| taacaacttc | gccgtctgga | gaatatacgt | tgtaccccaa | atcaccattc | acactaactc | 960 |
| ggtcagcctt | ttcttcgtca | ccatttgtgt | cttgcaatga | tacatattct | tccataaccg | 1020 |
| tcttcattcc | agcatacagc | ttgttttcat | tacccttatt | ggtaaactta | cggttgtaaa | 1080 |
| cattaaacgt | gattacgtta | acctttcat | tatgctttac | ttgaacacga | atagagcctt | 1140 |
| taataatttc | ttcgttattc | ttatcagtac | caagttccaa | agatacttct | gataatgtac | 1200 |
| caacaacagt | tagtgcatta | cccttcaatt | cttttaattc | aacagccatt | acaatttcct | 1260 |
| cctagttgtt | tttcattact | attatagtat | atcatttatg | aatatttgtg | tcaactatt | 1320 |
| ttataagttt | gttgcaaata | atttttttgtc | gaatggatat | tcctcgtctt | caccagtaat | 1380 |
| aatatacgtt | gacatcattt | ccataaagtg | taggacattg | tcattctctg | acataacttg | 1440 |
| ctcagatgga | gttttagcta | agtattgata | actgcaataa | tcttcaaaaa | agtaattatt | 1500 |
| gttttctgaa | ataaatctct | taacatcttc | tactctttca | tctgcttcat | gtccttggtc | 1560 |
| ataatacttt | tcaaaaaata | attgcttaa | ttcgtctagc | gtgacgccat | ttaacgcccc | 1620 |
| ctcaaattta | cgatacatcg | ttatctctcc | agtcataatc | cacattatcg | tgatattgaa | 1680 |
| tttcatattt | tttagttgtt | cccataatct | tagttttaaa | gtcatgcgtt | ctaacgacaa | 1740 |
| cgacttctac | tggaattcca | tacgtttcag | caaataactt | aaatgagatg | tttgctcctc | 1800 |
| tatcaatagc | ataattagta | aatccgttct | taacgtcata | tacatgtttg | ataaggtcat | 1860 |
| ctttatcaag | cacaacgaaa | tctggtttat | aagtaattcc | tctaatacta | attttgtcat | 1920 |
| taataacgtt | tttttctaat | aatttaaatt | tatcgtgaac | aataatttta | taaccagaat | 1980 |
| tttctaagaa | tttcttgtaa | aagttatatt | cttttctggct | atcaaacgtt | atgccaccctt | 2040 |
| ctttaatctt | ctttccgtaa | tgctgtaagc | ccataattag | catactcctt | atcatttgta | 2100 |

```
aaccatctat tggtcgcaat tgaaaagtgt gtcccatttt ctggtttaac gtttgtattt    2160
ttaatttttt ctaagcattc ttcataagtc ccaataaagt caaacctctg aacaataagc    2220
tctggcatat cattagaagc cgtgattact tgacataaat catacaagca aatagacttt    2280
tctttaatat gaatgatgtt gtctttaact tcttccatac aattctctcc taataattat    2340
tatatctttc cgatacgtta atactattat acaactgata ttcaactttg tcaaacatat    2400
gtagaataaa gagttattct ttattcatta ttaatctttt caatgctatc ccttttaaac    2460 attttttgatt cttctgaatt attgattgat acaattaaca tacaatctgt ttcctgacat    2520
acatcaaaca catcggtata gccaactaca actccataaa tatttgtaga cttaactcta    2580
accaaatcac caatattaat catattaagc atacttcctt atatttattt gttcaatgcc    2640
gcttgcagaa agtaaaatat aatttcctga ttcataatat acctttgcat ttcctgcgat    2700
agttgtctta atgttagtaa ttcctttatt acctacgcaa tacgtactac caacaaaatt    2760
tattgaatct atatacatat tactagtaca tttaattaac attattccac ctcgttgaca    2820
ctgatatgaa gtacagttac agcaatactc atttcttttt taataaaaag ccttctaaat    2880
ttcattgtag acttttttatt gattaggctg actccatcaa tagacttgta tttttttgtca   2940 taaattaatt cgttatagaa gtcatcgtcc ccttttctaa ttatgtcaat atcaccatca    3000
aacatatcac ttgccttatc taaacaagct ctaagcaatc tatcattaga cataattaac    3060
cttaatacag aaatatcaat cttctcatta ttcacatagc attttaccaa taggttacta    3120
tagcctttct taatcatatc ttcaataact tcttgataat tagattcaaa tatcaggtat    3180
gattcttgtt gtacttgatt ctttaattca ttcacattca tatttatata tcctcctaat    3240
tatattaatt ataccatatt atatataata agtaaacgat aatattatgt taacatcttt    3300
tccacaatta taaaatcaaa cacacgttca gcaaccacag tttgtaatgc gatttgtttg    3360
agcgatacag tctttgccta tcgaattaaa aaagaataca cttattcatt agacgatagc    3420
aaagacaagt tagttcgcaa cgctgatagc cgtcgctcta acagggtgaa ttatctttga    3480
ttggtatttc aaccaatcac cagcttttaa cttccatgct tatccagtcc cggaagcaga    3540
actttcgctc tatactagtt tgcctaaagg attgtgttaa gtcccagcgc ctattaatag    3600
taaatatatg aactcatatc atacagtgac tacttagtac gactgggcga acattagccc    3660
aaccattcca tctttcacat atccatttca taaggactta gttttcatca tacgattgga    3720
ggcttttgga atttttaccc cctgactcaa tcaacactac ttcaactcac ctaaagcaat    3780
gccgacacat accatttgtg tgcgcggtag gttatccgct tgaatctgtt ttattaaaat    3840
gtcataaaaa cattatatat ccatataatt tgaaagtcaa ataatatttt tgattattta    3900
tgttgactta cagaaaaata tgttgtatac ttatctaagt agaagaattg gaggataaaa    3960
gtaatggatt ttgataactt taagaaaaaa gttgaagaat tggggtatga agcagtaggt    4020
tatggagata agtttgcgt ccttaatagg ggaagaattt taatcactat tgacagtcaa    4080
tacgaactaa aagttaacga caaagaatat tttaaagtat taccattatg taaagagcta    4140
ttcttattgt cgtctgaatt atcttttagaa gaaacagtat ttaataggta ttatatttta    4200
attccgggaa tcgcaaacgg gtcaaattat attaacatta atatggattc aaatgaaatt    4260
gttatctgtg gtaaaggcag aattgatgat aatgaattta ggacggcttt cacatggaaa    4320
gaaattgagg atattagaaa tagactagat gtaattaatt ggagtaatgt aaaatatgaa    4380
cgagttaaag attagaggat ttctaagccg taattatttt gtcaagtcag atgaaatcat    4440
```

```
atacacatgg tggagatatg atgtaaaaga atatctacta aaaataaatt tcaagcaaat    4500
taagaaaaaa gaaattactt tgggaagaga cgattcttta gtatgctata agatggatgt    4560
ggggcgtagg gtgtttgatg tatgcgaact accaattgat aaagacggaa tattgacagt    4620
tgacgatgga ttttttgaga aaggtgatat taaagagtgg aaaagcagat tgttatgagt    4680
ccagatgaat atgaggagct ggaaggcgat tctaatagat tagggtatgt catgagtctt    4740
tttaagctag aaggtaacac aattttcctg aataaaagtg aaattttatc tatggttctg    4800
tcgaagaaac tggttgatga gggctatgaa caagtcacgg ctatctatgg tagcggaaaa    4860
atgatttcat tagaaggttt aaatgagaaa ggacagtcga aagaggtggc attgtcagat    4920
tatgacatta agaaggata acgagagtgt agttccagaa cactaccaaa aagatggtaa    4980
agatttatta tctcaccttg aacatatttt accagaagaa gaaatgcgag ggcatatcg    5040 ttttaatatt atgaaatatg caacacgagc tggtcgtaaa gatgatatta ctttagaaat    5100
tgataagata actcaatatg caaaacgctg gaagcagttt gagcagtcga taaagaaacc    5160
atctccatca atcaaagaca gtacgtggtc aagaaaaggt ggccttcttc ttcaattcac    5220
ggataaatat tataatggtt gggatatttt atatcgtatt gataggacta tgccaaatga    5280
tggattatgt cggttgtttt tatcaggagg tagtccagcg tacattgatg acagtggatt    5340
tgtttccatc ggtgattcgg taacgtacta cactaaaaaa caattaatga cattcttcaa    5400
tgagtgtaag gacgataagt ttacttgttt agagatattg attgaagaag cataaaatta    5460
ggaggaaaaa tattgttaat taatatcatg gccgcgtttg gggccggaaa aagcacgtta    5520
gtagatattt taagcaaaga tttagaagca acaaaatatt tagaagaccc gtacgcgatt    5580
ccgattttga agattatta ttctggtggt aaagaaacac gcaaaaagtt tggattccca    5640
ctgcaaattg catggcttga cgagcgtttc tcacaactga gagaagctgt cgtacaaaaa    5700
cgtgctgtta tggattctaa tttggttgca gactcaattg ttttataaggt tatccatgac    5760 cgaggtgaaa caacagacca agaatactac ttatacctaa aactgttgcg ccatatgctg    5820
gattctgtta gtgcagaacc aaaagggcat tatccagact tatatgtatt cttagatatt    5880
tcacctgaaa atgaggttaa gaatatctta gagcgcaacc gtgagatgga aacagcagac    5940
cctgcactga ttgaatatta tcattcgatt aatgaaggat ttaagaattg ggccgattct    6000
tatagtgaag caccgattgt taggattgac aggaataaat ttgactttgt gaacagtatt    6060
gacgacagaa ttgctgtttt aaacattatt gaagaaaagc tggttgaatt aggctacttg    6120
acagattcag aatttaaaga aattaaaaat acaagagaga agcgaggaat tttagaatga    6180
agacttttgt ttcagcaatc acattttat ttgcggcagt atttatggta ttttctatg    6240 ggttggtagc gtttgtactt ggtgcactat ggggaattag tgtaacattc atcttagcgg    6300
tacgctgtgg gattactgcc tatatttgt caattgtgtt gccaatgctt ttggttccag    6360
ccgctacaca agaataatat taatcgcacg cttgttagcg tgcttttttt atgctataat    6420
ataatagaaa caggaggtta tgaccaatga gaatgataac ttgttatggg cctaactgct    6480
ataaacaagg aataaaacac cctaagagcg aactaacaaa ttttcacggc aagaattatt    6540
gtgataagtg tttaaatgag gtaatgaata actatgagtt tagacaatca ctaactgcat    6600
tgctattaag agactacaaa agtaattatc tacccggtat tgtaatagca caaatcaaga    6660
aatatcgcaa aatcggaatg acatatgaag gaatgtataa tacggcacta tggattaaag    6720
agaatcaaaa tgttgtattt gaaaataaat acgggattgc cttaattaaa tatcattatg    6780
ataatcattc atcgtataaa gagaacagta cgaacagtaa tcaagcaaag gttacaaatg    6840
```

```
caaccgtggt tatatcaaag ccaaaacgta agcacaaaca aatcagagaa attagtggag    6900
atgatttact tgattaataa gaacgaatta aaagcattaa ccccacaaag tcaaatcttt    6960
ggggtattag gtgtattatt aaataatcca gaaaaattac tttcagatga tgtatttta    7020 gacaaggaag atttccaaaa taatgtccat agaattatat tttttgcaat taataatatt    7080
attaaggaat cagaacaatt aaaagaaata tctgcaattg atgttacac ttatttaact    7140 caattcgaac agtatcattc aatctttacg tcatctaaag ggattgacta tgttcagtct    7200
gcgaaagata acgccaatat tggaacattt aattcaaact atcattattt aaagaaaatg    7260
acggttctta ggaagtttgc agagaacggg attgatatta gcgatattta tgatattcat    7320
acggaagata ttaagctatt agaagaacag cagaaaagac ttagtcaatt atcagaagaa    7380
gatattgtta accattttac gcaggtagta agcggaatca gaaatgaagt ttctgattgg    7440
caaaacaatt cgtcatcttt ctctgccggt gatgatattg agtcgtttat tgagcatatt    7500
aatgatgaac cccaattcgg ctatggattt aaagatacat ttatgaactc attaactggt    7560
ggtatgcaac tcggtaagct atatttacgt tcaatgaaaa ctggtggtgg taagtcacgt    7620
cttggtattg cagatttaat caatgtgtct gcaacagaac agtataattg cacaataaaa    7680
aaatgggtca agaataacga cgtagaaccg tcattattta tctcaacaga attagataaa    7740
gatgaaattc aaatgattct tttgtctgca attacaaatt tagccccaga aatcattaga    7800
cgtggtaatt ttgaccccga aactaagaag attattaacc atgccgctgg cgttttacat    7860
gattcaccgt taatgttcaa agaaatccaa gactttgata ttgatgatat tatgtcaatt    7920
attgatgaat acgtgtttaa ctatgatgtt aaatatattg actttgatta tattcaggcc    7980
gtacctaaat tactacgttc tggagctaag ttatttggtg gtagagacgt tcgtgatgat    8040
agaatcctat taacattaac agacaagcta cgggcaaaag ctaaggaact tgatgtgtat    8100
atcatgtcat caacgcaaat ctcgccttct ggagaaatgg attacgaatc gtcacgtaca    8160
gaacgtgccc tacgtgattc aaagtccatt gccgataaga ttgatgttgg catgattgtt    8220
gcagaagcta attcaaaaga taagaaaaac ctagagaagc tgattaataa taccgatatt    8280 aaccccctatg gattagaacc taatatgggt aattttatt ataagaaccg tttaggtaag    8340
aagtcaattg tcatttggtc ttatgtgaac ttagggacgc tatacagcta ccctttattt    8400
gtgactgatt atcagtataa cttagttgat gttccacgta caaagattga ggttggcagt    8460
gatggtagtt ttggtatcaa ggaagacctt gtattttagg aggtaaagat agtggaatac    8520
tataaaagtg acctaatcaa agtcataaaa tattatgggc ttgattataa agagggccat    8580
gattactatc aattgagaac atattgtcac catcaagacg gagacgggaa ttttaaactg    8640
tacgcatatt ttaatgataa tgatgttgtg tctttattct gctattcaaa ttgtggttcg    8700
atgaacttag taggatttat tatgcactat aaggaatgtg actatccaag cgcgcaatct    8760
gaactagata tgattgttgg caaacgccag atgacgggat tcgtagcgca ggacttatat    8820
aatccggcaa aacagtttga aaaagagac gaaagcaaaa atatcaagga tattaaaaga    8880
ttaagcgctg ggatattaag cacttatagt aggtacgcat acggtggctg ggttaacgag    8940
ggcattagtg tgaggacgca ggcaaagttt ggtatcgat attcaatacc agagaataaa    9000
attatcattc cacaggtgga caaaaacggg gagctaatag gtatacgtgg gcgtagtctt    9060
gacccgtatg aagttgagat gtttggtaag tatcggcccg taaggttcag gggtcaaatg    9120
ttgtcatatc cgacaagttt aaattggtat gggctttatc agaataaaga atccattatt    9180
```

```
aacacggggc aggtaattat tttcgaatct gaaaagtccg tcatgcaatt agatactatt    9240
atgaacggaa atggtaatgg gctggcgtta tctggctcta gtatatctga ttggcaaatt    9300
gatgaattga tgaagctaaa tattaatgaa gttgttgtcg gtcttgacaa agactacaaa    9360
gatgaagctg gatataatat tcatgctaat atgattgtca aatgttcaa aaaactattg     9420 attaggttta acgttactgt tatatttgat gatgtagatg gcttacttgg atataaagat    9480
agccccactg actgtggtag agaagcattt ctaaaattaa tgagaacaag gaaggtaatg    9540
ttgtgaagat agtagaaagt gatacggata ttgttaatga acaagttgaa ggatttgatg    9600
ttgatattgt ttcaaaatcg gtaaatgata cggttaaaga agcgattgaa tatcgaaaga    9660
aaaatgtatg gggggcaaat aatggtgttg tagattttaa ttgcttacca cataagaatg    9720
agttgaatgc aattgcaaaa gatttgcaca gcaataaccg taaggtagca atcctagtgg    9780
acgtcgatgt agatggttac atgtcagcgg caattatta taaagccatt aagtctatca    9840
acaataaaca agacattgat atgctgttcc cagatgtgaa attacatggt atcaaggcta    9900
atgttggttt ggttaatgat gaatacgatt atatttttg ccctgatagt tcaagtaatg      9960
atttacaaac aatttctaaa cttgaaaaaa acaagagaac taaagtagtc gtaattgacc    10020
atcatatcat agagcatgag gattatatta ttgataatcc cgataaattt ttaattgtta    10080
gtaatcaata tcaagactct gaactgaata agaattaac aggggctggt atgtcattac     10140
tggtttcaga attgtggaga gaagactacg acattgaagc taactttgac ttagccgcca    10200
ttggtcagat tgccgatatg agtgacctta tgacgaggg gtatttaat attgtcaaaa      10260 aaggattgtc agaaacaact aatgaaatgt tattaacgtt ctttaaagat gatgaagaag    10320
tacgttcaat taaacatatc caatttactc taatccccaa aataaacgcc gtgtcaagaa    10380
ttggtaatca tgaagaacgt cagctaattt tcaactcgtt cattgacaaa ggtgaagtaa    10440
tgccagtaag tgtcagacat aagggcggtg atggtaaaat gtacaccgag agcgttgaca    10500
tgaatgtata tgaacgagca atagtgtct tgaaaaaggt taaggggcgt caggatagac       10560
tggtaaaaag cgcgttaaag gacgttgaat ggcttagtga tagtggttct gaatacaatg    10620
caattgtaat cggggataag tttagtaagg ggatttctgg cttagtagct aacaaactgt    10680
tggggcaaac taaacaaccg tcgctggtat ttaaacgcaa cggcgacagg ttagatggta    10740
gtggacgttt tcctgaaaat ataaatggtc ttaaactact aaaggatatt gatggtgtat    10800
tcgccgctgg tcacgagcaa gcgtttggag ttggcttcc agaaaataaa ttcagtattg      10860
tatcaaaggt ggttaatgtc gcgtctaagc agtcaccaga ctacgtatat agggttgatt    10920
ctgcatatgt tgatgaacta ccaaccattg aagaaattag agatatttat caagagtctg    10980 ttattttag aggagcgaaa gatgagatta agtagcgat tcttgggcta aaagtagaca       11040
aaaaagatat tgttttaaag aataattgga cgaaaattaa gattggcggt cttgtcatta    11100
atgactttaa cacaacagac gatatgaagg agtatattaa taagttcggc gataagtgtt    11160
ttagtttcgt gtgttcggtt gggttcaatt tctggggaaa agaaccgaca ccgcaactta    11220
atgttgataa aattgtaaaa agcgatggag taagagttaa aataacaaaa gataattttg    11280
tgttctgaaa ttagaggcaa taagcctctt tttttatttt acagattttt ttattttttg    11340
agaaaaagtc ttgactttt tccgccgata gcagtaaaat atagttataa taaagaattg      11400
aagtgagtta aaaatggaaa ataataaaaa tgttatgaaa aataaaatta aacatgaagt    11460
ttggcgcacg tgcccagaat tttattggat tcaaggtagt aatcttggta gggtgagaac    11520
aattgataga tacgtgtcga atggtaaagg tggtaatcgg ttcgtaaaag gacagatttt    11580
```

```
ggccccacac tgtctaaata atggttatat gcaagtgacg tttagtgtat acggaaaaac   11640
aagcccccag cttgttcacc gcataatcgc ttcatgcttc attccaaatc caattggttt   11700
gccagaagtc aatcatcgca atggtgataa ggctgataat cgactatcta acttggagtt   11760
ctgcacccat aaatataaca tgcaatataa agaaaaacat ggggtatcct ccgcagaagc   11820
tgtaggttgt cctattgttg cagtcaattt aaaaacatgg aaaatattgc ggtttaaaac   11880
tcagttggaa gcgagccagc aacttggaat tagtcatgga acattggca tggttcttgt    11940 aggacgatat aaatatgctg gtggctacta tttcgcaaaa gatactggcg gtgacttaaa   12000
aatcgacaag gataaattat gtgatattga ggttatcaca gttttagga gcggtgtgtt    12060 tgcaattgac ctaaaaacac aagaagtatt gtattttcaa tcacagacca agcttctcg    12120 tgagttaggg gttacaagc aaggaattaa tcgtgttctc aaaggccaat acaaacaagc    12180
cggtggttat tggtttgtaa agaagataa taacgcggta gaagacacta gagccaaatt    12240
tggggacgct gtagctgata ggatttcaga attaatgagt gaaaagaaa taaaatcagt    12300 ataaaagcg tttgacaaaa gcatttcata taggttataa tataaaagt ggaagatagt     12360 aataaatcgg aggtgcaatt gatggaatat aaggaaataa cgaaggaaga agcacataat   12420
atgacagtta ctggttataa aaccagtaaa aatgttagtt tagattttga aaaacgaaag   12480
cttatgaatg atattgatat tcttatcaaa tatggatttg acgcaacttt tgcggtatat   12540
aaaaatgata tgtgtgatgg atattcttat aaagaagatt tcttgctaaa agattataag   12600
gatattaaaa agtggctatt atcgcttgga tatagtgtat cactattccc accggcttta   12660
gttccatgta atcaacattt tatgacagtt aaatggaggt aaaaataatg ttaaaacagc   12720
ataaacatca ttggctacga gtatctaata aaccttggtt ctcatctttt ggagcagaag   12780
ttgtattaga atgttctatt tgtcataggt ttattaatgt tagtgaggaa gaagtaagta   12840
attttgaatc taaaactaga ttggtatatt aggaggaaga aataatgaa atgaagaagt    12900 tctttagtgc gttatttgat gatacgggca gtaaggtggt aatggtcaac aatcaaaagg   12960
aaaaaattaa agaatcgcca gcgggatttt cgtggacgac gttaatcttt ggattttggc   13020
ctgcattatt acgaggtgac ttttttaggggg cgctagtcat tatgattatt aatgctgggg   13080
caaactttaa tcctgtatta tatgtattgt cttctgtttt gattgctatt ttttataatt   13140
atgtatatat taacagaaaa attagtaatg gatatggcgt gccaacgaac aacagtaaag   13200
aattattaga aaaacacggg tatgacgtaa acgtaaatgt gatgtacagt ggaggtgata   13260
acgattagta agattattaa aatgctatca ttactattgt catatgtgat tctgctgatt   13320
attgcatata attttacaga tattttacaa caagacggtg gctttaaaca aacgctgttc   13380
ttcattgtgc taacaaccat ctacatctac attatgtcat ctattgataa agaaactttt   13440
agaattaggt ttagcttact tggagtgatg ttgtatatta ttggtgttgc cggaatgtca   13500
ctgtgtggaa tggaaaacca aaatagcgga attactgcac tatcgtcaat tgttgcaatg   13560
tcattcttga ttgtgggggt tattaggtta aatggatagc tataaagagt tcaaaacatt   13620
aagtgcttct aacgcatggg ctaaagagcg acaccttaca tggtacacta acttcattaa   13680
gggtagcgga tataatccgt tagatggttt aaaagaatat gccggtagcg acgtaaaata   13740
tatcataaca aaggttggta aaacatacca gcttttttat aagaaggatg attaatatgt   13800
caggatatgc aagacgaggt aaaaaagtat attcatactg taatccaaaa gagttttcg   13860 attttttacaa tcatacaagt gttagttcaa tgatggttaa attagatgga gaatgttacc   13920
```

```
acttaactga taatggattt agaaaaataa aagatgacga cgttgtagtt tttaacaaaa    13980
ataaaaacta ttggtcaaaa gaagataatt ctattatttc taaggacaaa ttcaacagcg    14040
aatatgagcc tgtagaaaat attcctaata ttaatggatt cttaatggag tttaatttgt    14100
attttgattt tcatagtacg ataaaagtat ttaaaaaaat gttgaaagaa cttgataatg    14160
aacattatta tgaaaacgcc gacctaaaga atcaactaca atggattatt ataatcagg     14220 acgtattctt atatgcgtta tcataattgg aggtttagta tatgagtaaa aaatacctaa    14280
caagcaatga aggatatggg gaaggtgttt cagattttt  atcatctgaa ataacagaca    14340
caatttcaca tattatgttc ggtttaaatg aaaaggaaga tactaaatat cacgttcaat    14400
ttagaagtgc gtatggtgga atatcgcata aggattctat ggaaggtgca aagccaatta    14460
cagattttca taaggcccta ttagcattta aaagtaagca cgcagttatc attcaaatta    14520
attttaatga cgcaatggta gatttagaa  cgcgtaagtt atgtgtaagt gtggaaattg    14580
gacaaaatga aattaatgag gagtttaata tcatggcagt tcatcccagc gaggcattct    14640
ttattgacta tgatagtgat aatgatgtag aatctattaa gaaccaagta aaaaaggcta    14700
agatgattgg attttttgat ggaaccgtta atgattatag gtagttaatt agaccctgtc    14760
cagggtcttt ttttatttt  taaataatta gcttgcttta ttattattca tggtgctata    14820
attaatgtat caaataaata aggaggaaat aaaatgttaa gcaaagaaca actttataaa    14880
cagggtaata tcattaagga caaggacaa  tattatatta ttgttatgta taaggggtta    14940
ttcgtatgtg gtgatataga tacgctcaca catttagaag actgggacat taacaatgac    15000
gcagattttg ctaactcact gtcggaacta tctgaaatgt tatggactag ggacgataga    15060
ttagttacga cggtacaatc aaatcatatc aaggaattaa aagaatttaa aatcggagaa    15120 ataaccccgtg ataattctat gaataaatat attttgtggc aaaaaccgaa aggcaaaaaa    15180
gtatgggtgc ctttagaagc acttaaaaat catgatttaa atgagctatt gcatatcaaa    15240
tggaatcgtc atgagaattg ggtagaaaga accccctaaca aagaattacc cgttatcgaa    15300
tttgttgcat tgacagaata ggagagtgat tataatggct ggaaaattag caattagtta    15360
ttattatgat gtgatgagag gttgtagtgg attagcaatt catcaatctg gtaaagaagc    15420
tgttgaagaa attgaacggg cggcagatgt taactttaat atgccagttg ttaaaaagaa    15480
gaagttaaga ttaacaaaag gccatgcagt tacgattggt tacgcaatga ggtattttgt    15540
ggcacgattt ttagatgacg aagaaataga gatttacaaa aatataaag  acaattcaat    15600 gtttagtcaa aaagaactta aaattgtaga accagactaa aaaggagaat aaaaaataat    15660
gtcagagcgg tatgacgaac agccatcaag aatgtgggac aaatacagtg tgcgggtatt    15720
tgctgtttca gatgaagatg aagctatcca aaaattatat tttgataaag tagaggaagc    15780
tggattcaac attgaaaaca gattagatag tgatggagac aaaggaacat atattgacaa    15840
ctttgacttt ggagacatgc caaagttaat gagggcgtta gatgaagacc taattgtaac    15900
ttacaacgga aaagaatttg aagttaccat ctatgacttg ccaatttgtt aataacagga    15960
gggtatttat aatgaatttt gaacaaatgg ttaaggcact tttattggga aagccagtaa    16020
aaagagaaaa ttggcgaatg aatacccaca taaaaattgc aaaaaacgga gataccgtag    16080
atgagctggg ctatccgttc acatttaaca agcaggatta tgaggcaaaa tggaaaatat    16140
ataaaccact aactttggta gatgagagtg gcttgatgtt atacggcttt gatattgatg    16200
gaaataaggt gcaatacaga gttgtaagtg atagtgggga ttatgaaatt gttgatgttg    16260
agtgctgggc ggtaattgct aaaaacatta gtgcagataa cttatattca acaattgatg    16320
```

```
aacttggaat ggagagagca tagtggaaga aattaaatta attgaagaat ggtcaaagaa    16380
acgaggttta gattctagta ataatgataa acaactcatt aaactagtag aagaagtcgg    16440
agaactttcg gaagctcaca acaagggctg gcgtgataag cagattgata gtatcggaga    16500
tatttttgtt gttctaacaa tctatgccct gcaaaatggg ttacacattg acaattgtat    16560
taaagaagca tacaatacaa ttaaagagcg cacgggagaa actgtaaatg gtgtgttcat    16620
caaagaggag gataaacaac tgtgaagatg tcttttaaag aagccttaaa atatatggaa    16680
aatggcgggg ctgttaggcc aagcacgtgg gacaattcgt atgtgttcat tgatgatgaa    16740
aaattcattg acgactgtgg aaataggggtt tttatgagtt atgaagatat tgttgctgag    16800
tgggagctaa tagaaacaga caagattaaa gttggagacc gactgatttg tcgtgataaa    16860
aatacaaatg ataaagcgtt cttctatata gtatctactg tcggtaactt ttttgcgatt    16920
aatgttggtg aaggcgcgta ttatcgttct aataatttta aacggcttga aagcaaattg    16980
aataatagct acacaattgt tggaaaatgg ggtattaaag atttaatgga ggaaaaataa    17040
taatgaataa tagaaaaata tttgatttta ccacaaaaga atatgaacaa tacgcaatta    17100
atcgaaaaat tattgaagaa tcttctttgg aagaagcgat agagaaacac ggtattgata    17160
tggaaaaata taatgtaact gagatgacat tggacgagct tatcaatact cttaacagaa    17220
ctgacaaatt ttttaataaa aaagttccgc cattagaaga acgaagaaaa aaatatgcaa    17280
attaccgtgg aacgattttta gtgaccaatg ttgcagacca ctaaaaacta gaataccgtc    17340
gttataggat ttgtggcgtg ttaaaatcag aataaaatta ccattttatg aaaagaggaa    17400
gataatgagc tatgatgtag agttgcaggc gaaaattcaa gacgttaata aatgggtaga    17460
acttggagat tcattcaata ttacttttaa cttggctgat atgttccacg agtgtgtcgg    17520
ctcaacacca agggaatggg atggaatgaa tgctggtgag ctagagccag agctaagaaa    17580
agcgattata gatattggcc ttaacgcaga atactataaa caatttgaag ctaaaaacgg    17640
ctggggaact attgatgggt gtctgcactt tatgagggga ttagcagatt gttgttatca    17700 ataccoctac gccactgtta gaacaagttg ctaacactta gcgtctgtat caaatatttt    17760
aaataacagg ttgacaaagc ataccttatc tggtatgctt ttgttataga aagaggaaa    17820 taatatgagc aaatatgtaa tcgcactaac cgatgatgtt gaaattttag atggtgaaca    17880
gtatgacacg ctagaagaag caaaggcgt tgctactaaa attttaaaac aactaagctc    17940
tgatacctcc aaaaatattg acgattacga agacaaagta tgtggctatt tagatgatga    18000
agataaaact attgataatt taacaatttt agagattaac ccagctggtt tcccagattt    18060
tggagatatg attttttgatg gcttagaaga ctattgtgta agtgaaggaa acctagatga    18120
aaactaccca gaaggtgtca caaacgaaga actagttgaa ttaaatgaac ttgtaattaa    18180
gtggctaacc gataaagggt atacacctag ctggtatatt atagaacctg tatgtttagt    18240
agaattgggg gataaataaa tgaaagttga ctatgatgat attaaggaaa taaatcccgc    18300
ttggaaagtg ggagatgtcg tccattccgt taatgataat ttatatttgg tggctaaggt    18360 agctgatttta aatgaagaag aaagcgggta ttttctatac actttgattg acctagaaag    18420
tggctctagc ttagggagct gtgaaacaat tgaagaatta cagttttgtt tttatgcgt    18480 tggtgataag gttcttaacg ggacttttaa atacattagt gggaacgacc agcaaagggg    18540
atagaaacta tgattaatgg agatgagatg tgtatgcaaa caacaggcga agaacctagc    18600
gaagaatcta acgtgaagaa agcgttcatg cacaaagaag aaaaaatttt agataagatg    18660
```

-continued

```
ggctacgtgt ataatcgaga tattcatgcg tggtggtcag atgacttaga ccagttacct    18720
ttgctaaaag acagggaagc acgtgcttta gcagatgaaa ttattagttt tgtccttaac    18780
tgaggagcta gataaaatgg atgattattg ggttggagag tgtccttttg atggcggaga    18840
tttatatgga gattcagaag gtcatgtaag ttggtgtaat atatgtggta gagagtttgt    18900
tgatggggtt tttaatggca attaaggaga tggcgataat gattaaattt agaggggttc    18960
cactagatag tgatgattta atttatattg acgatgttaa ttttaataaa cctttttgtct   19020 acggaaatta catcaaatat ggagataacg cagtaattgt tggagacgca cttgaggttg    19080
gtgaagatag attttggccc tcttggtggg ttccggtaga cactaagaca gtagaccaat    19140
ttaccggcct gaaagacgtg aacggcaagg aaatctatga aggcgatatt attcagtata    19200
gtgaccactt ctatgggtat tccatgggcg gagtgacaga ccttgaaact gaatatattg    19260
gaattgttgt caaaaataat tggaatttag ggatttttaat taatagaatt agccacacag    19320
acgcacatat caatcattat aacgccaaag agtttgtgcc attttgtgag tttgatgacc    19380
cagaagcaga cgtattatta aagggggatg tgcacgctaa cccggaacta ttggaggagt    19440
aaaaatgaag attaaaactt tttggacgaa ctgtacagag gactatgaat ttgatgataa    19500
agtcaatcaa tttattgaag acaagcagat tatccagatt tcatcaagtg atacaatatt    19560
accatatgaa gaccataatc atacgctaac tgtactctac aaggaagaag acatagatga    19620
agacttttag ggtagcaaac cactggttta atgatagcgg agattgctat atacctatga    19680
cttaggagga gtaaacatga ctaaaactta tcacaaaaca actactatca atgctgaaca    19740
gttcgatgga agcgatgaga tggttaataa gtatgacatc gaagtggtcg aggggggatta    19800 tgccgatgat tatagtatgc cagaagcagg accagcgcca tattttcgat atttttatgcc   19860 tagtgggtat aacgagatat atgtcggtga ttggattgca actggtgtaa aaggcgaaca    19920
ctgggcaatt gcgaatgaca tatttaagaa aacgtatgcc gaactgccag tgattcctaa    19980
aaacgttgca aattatcttg aagattgcaa gcgggcaaaa actactatag gaacatcttt    20040
atctggtaat atcgtgttgt ttagtcatgc taggtcacat aatatgattc acgacatatt    20100
aagttggctg tgtccgtccg ataatcaaaa tctgtttgct cgtgcatggc tagatggtta    20160
tgttataaag gtagagccta acaatgctta gagatatgct taataaagac gacccagtag    20220
ctaagaaagt gttagcttat caagatagta aagagtttaa gaaagaacta gacgccctat    20280
cagaaagagt taggcttgga ttaagtccag aagaatataa taagtataaa aaatctaatg    20340
agaatggtga aaaacatgaa atataaagaa gaaatcaatg gcattactgt tgagagcaac    20400
tatcctatta agtgcggggt agttaaagat atgttagaat acggctatga taacggtatg    20460
aggaaaatta ttattgatac gccaactgcc gatgagaatt ggtatgctgg agaagatact    20520
gtagaaggat taattaaggc acttgaaaag ttgcctaaag agatgtcggt tgaatataac    20580
tatgctggaa tcggggttga agcgtcggca gtgcctgatt atgatgaagg tgtctcgcat    20640
atctcttttc aattagtagt ttcagattaa ttttttaaatt agcatttgac agcacattgt    20700
gttagtgata tagtttgttt actaagtaat taggaggaat aaaaatgaaa tatagtatca    20760
ctgatataaa agctaagatt gaatctattg acgatgacaa cccatataag tctcttttga    20820
caaagcaact aagtatttta gagcaggaaa catgtgagtt ctgtcatgaa ccctacaaga    20880
atatggttga tgaagcagga tgggaccttg ggatagaatc ggacataagt tttggcatta    20940 aatatttga  cttagtaatg tctactggca aagggttctc tagcactcca gctaactact    21000
gtcctaagtg tggtagaaat ctatttttaaa cttgacaaac aatttttaat atactattat    21060
```

```
tatttaataa ggagagataa ctatgaaata tggtgaagct aagaagcaaa tcaaagcatt    21120
atcaagtaag tacgatattg acgtgagtga tggtgatttt aatgttgtat atagggaacg    21180
aggcaacact gcctatgttg ccggttatga gcgatataca tttactattt atgacgaaga    21240
tattttccca aagcttcctt tcagtaataa gctttacatg attttagctg agcttgcgat    21300
gaccccgtta gataaacgcg aagaggataa aaatatttt attcatgtgt ttaaaggaga    21360
agatgggtat ttaaatattg ttaataatgt catcaatagg attgagatta ttgataatcg    21420
tagtgctgat ggattcaaga ctgaatttac gaatgatgag attaatcaac ttaaaaaacg    21480
tgatgatgtc ccactggatt gggataaggt aactttagaa gaagtggact aggagaagta    21540
atatgaaaat ttatatctta tcacataccg ctgtcggtag ttgggaatcg gaattttgtg    21600
tagatggtgt gttctcatca atggaaaagc ttaatgccgc aaaactaaga atcaaagacg    21660
atttgccgcg acttgttgat acgtgtgacg gaaaaattga cccgcatatt acttttaaag    21720
ttagagaaca tgaactagat aaagagttct atgattttg gttaagctac tgggatatta    21780
tggaataaag gtgttggtgt cattgagtga tgatatattt gaagaaacga ctaaagtttt    21840
aaaagagaaa tatttgaaaa ataggcatga atttgatagc aaaagagcaa aactagccaa    21900
aagaaataac aaactatacc ccagcttcat taaaaatcag agaaagctac tcagaaagta    21960
aaagcaaaga cactttttaat taagtgtctt ttttcttgac tataattctg ataaatgcta    22020
taattgtatt atagaatttt aggaggaaat aatattatgg aaaaagtgaa tattgtctct    22080
gttagtaact ttgacttaga tgattataac gaatcattcg tagcaaaaga tgtcagaaag    22140
gactttgcac aagggattgc agaatattta aatgaagcct attcaagcgg tgatagcttt    22200
gattattatg tagtaaagcc gcatgattat gttctaaaac attttgaacc ataaataaga    22260
tagaaggaag attaataatg ccaaaattaa atccatataa gaatagaaaa gaaagcttat    22320
tacccattat ggatatttac ttaaatgttc ctagcgaaat ctgggtatat aatgttgaca    22380
tgagttttaa taaaaacccc gacgaatgga ttcaaacacg agtgacatgc cctaagtgcg    22440
gatgaaaagg ggttgaaaga attattggtg cgggacaaaa gccccatgtt gtaaaaattg    22500
ataatcagaa aatgattaaa gaattttatt ttacacgctg tccatattgt cataatgctt    22560
ggacaattga cgcaacgcgt ccatacgacc caaagaccct agcacttagt gttgatgatg    22620
acctgaatga tggtattcaa gagttggata atgaaatcaa ggaaacaag agggataata    22680 aatgattaag acattagaaa aacaggcggt gtcaacaatt gcagaacccc tagtaagatt    22740
ctattatggt acgatgcgtt ctggaaaaac agaaaagtta ctgaacgact cactcgaata    22800
caagtataac acagtattcg ttttaccaga agaagataca ggtggtttaa ttgaatcccg    22860
tgcctttacg gtttctaatg gttggacatg tgattttgtt attacaccca ataatttt    22920 tggtattaac catttttag aaactgcaag atttttgac ctaatttatc aagattgtga    22980
tgttgaaaaa gttgtaattg atgaagcaca attttagac cccaattata ttaatagcat    23040
tgtaacggct tgccgctcaa ctaatacaaa gttggacgca tacggactgc taacagactt    23100
tcatggcaat gtattcgctg gtagccagag atggattgat tgtgccgatg agtctatttg    23160
tatcgaagga aaatgtgagt ttccggggtg tctaaaaaaa tcatattata attgtatgat    23220
gaagcaacaa aaatcccctg attccaacgt tgttgttggt gatagccaat atgtagtttt    23280
gtgccccgaa catagggaat tatataagaa agcgggtttt attgaagaat gaattatatg    23340
gcagaacaag cagtctctgg tgccgacatc atgtcttact gttgtgggtg tgagacaaac    23400
```

-continued

```
agaatgttta aacgagtatc tctagctgtt attggaagaa aaaatgttac agcacgatat    23460
aaatgcgaaa aatgtggcta tcagaatatt tataagtttc caagtagta atcagacccc     23520 ggcccatatt ggtcgaggtt attttatac gcataaataa gataaagttc ttcaaatatg     23580
tcgaccccat actaattact agttgattta aattatgtgt acaaatcaga aaaagttctt    23640
caatatatat atatatatat acgattattg cgtaattggc acttatttt ataagcacta    23700 aataaaataat cccgtgaaat ctcatataag acgtcgtaac aatttatatg tgtaatagtg   23760
ccataatgcc gtattatcgc ttaaaacaat ctttatagcg cattttgcaa tataaagcta    23820 tattcccgt atattttga aatttatgca attatctgtc attgaagtta tttaatggtt     23880
atgttgtggc cgtttgagga catataagta tgcgaggata ataaattggt caataattga    23940
atgctttcat attgcattgt aaaagcattg cctatgaatc tgtgtaaacc aaaagccacc    24000
aaataatatg tacccacaca caaagaatt tgtcaagata ataccacatt ttgataaaaa    24060
tatatatgcg cacaccacgc gccattacaa gataacgcat aacacacata cgctaaagca    24120
tacatattat agcgctcagc gcttatgaga aacacgcgca tatgtacaca tagaaaacac    24180
gcgcacacat acatgaccat ctaaccacga aacacgcgca tacacacata tataaaaaac   24240
acgtacacac atgtatatac acatacgccc caaaaacacg tatacatacg catatacacg    24300
cataaacaca catagggggcg acaatccctg aaaacacgta tacatacaca tacacacata   24360
aataaacata tatataggct ttaaacgcct gtatatcaac atttataagg tatgcgtata    24420
tataaaaacg ataaaaagct actataatat gtaaaataat taatataaaa acatgtagcg    24480
acaaaataaa cgccctaaaa cgttgatatt aaagagctta cagctatttt taatgcaaaa   24540
aaatgatact tttctactat aatatgcaaa aatgatttt taaataaaca aactttttta   24600
attttggggt tgattttaaa tatcgggggt ggtatattta aatcaatcaa gcggggggggc   24660 gaaaataaaa aataaaaaaa ataaaattaa gggttgacaa acaataataa aaaatgtaaa    24720
gtgtagtcat caagtaaagg aagggtgtaa agagtcatga aattaaatgc aaaagctgtt    24780
gagatgttgt tgcggggtag taatcatttt gagattgtaa gccagttgga tacgtacggt    24840
aatgggtcaa ttgttgaggt aaatacacgc ggtaagattt acaatgtcaa aagcaattat    24900
caaggtacta atacccacga tgttattatc gcggataatg ttaataaaga gattaagcag    24960 tttattcaa ttttaaaaga caagggctat caagaattat agggggggtat aacgatgatt    25020 aagaaagtta caaaaataga actcgaaaat atcgcattcg ataattatta tttaccatac    25080 gagttctta taaagtaaa tatgttagaa actatcgggt tactatttaa aggcaaaaca    25140
gtttataagg ttggaaacga atttacact gaaatgtaac ggaggtaaaa aacatgttgg    25200
taattacatt agaaaatacg ttctatattg ttatgttagt gttctcagcc ggtggtatgg    25260
tttacggggc gctagaattg ttccccacgc ttaaaaactg caagtttata aaatcatttt    25320
ttgaataaat aacatataaa aagggtgaat atatcatgat tctaactaac gaactagaaa    25380
cggtagatac tattaatgag acagctttac ggaaagcatt acaaaaagaa attaatacta    25440
ttaacgcatg tactgattat tttatggacg tatacaacac taaacacaat cactttacta    25500
tcttcgttaa cgagcttatc gagtatgact tagatattac tggctttact gctgaattat    25560
caggtaagac atcaacattc gatgatgatg ttctacttgc cgccatcatt gatgacagcg    25620
gaaattttga agagaaacta gccattaagt tggtcagtgc tatttatcat aagtgcgtta    25680
ccatactata aaatgaggcg taaccatgga aaaagggaa ttctacaaaa gactaactaa    25740
tgatttaaag gtgtggaaaa actacgtcat tagacgcgac gacaaagagt tgtatatcgc    25800
```

```
gactgcgaat aattatgttc gtgttaattt taaccgcaac gccgtaacgg tgtacaatga   25860
tttatatcgt gatattaaaa aatattatta cactgataat attgtaacat tgaccgcgga   25920
caaaatagaa tggatttttga aagataaaat atagcgacaa tgctacgcgg tagcaattta   25980
aaaatatttt tttaaaaagt gttgacatta ccaaaaaata gccgtatact ttaatcattc   26040
aataaggaaa gggagtttag acatgaaatt agataacttg aatgcacaac tggaatgtgt   26100
aacgaacaaa ctaatcgtta agatagaaca agccgacaaa acagaccgct atacttgcga   26160
taaattgcaa gccgcttgca atgacctact gattattagt acaaaattga ccggccgcga   26220
tagcgacaca actacccgga tggttagggt taatcataga ttgaaccgta tgcttaaagt   26280
taattattta ttttaaaaag ttattgacaa ctagaattat agggcgtata ctcaagtcat   26340
taaacaagga aaaggcgggc gcttaccatg aaaaagggaaa ttacgttaga tgtaaactta   26400
tcggacaatg atacggtaac agtaaataga actactacaa ccagttcgga acaaaccctt   26460
aaagagggga caattacctt tatagctacc cttgatggac gtaaaaagac ctttaatcct   26520
gaagaggcct tgttaaaagc ggggctagta acaagtgatg accccgataa cttttttccct  26580 actcttaaag cgactgctga gtttatgaaa ctatttgagt ttaaaactta cctgctatca   26640
tattcagaca acaacaaggt taagagcctg tttaatgagg ctcttaaaga gctagacctt   26700
actgttcaag atgtggcaag caaacttcaa gaccaaggcg ttacaacaac agccgcatta   26760 tatgaaaga ctaagcagga tattaaggaa ctattaaata actagataaa taaaaaagga   26820
gaacactagc atgttaagta aaagggatt tcttgaattt tataaacatg aacaggaatt   26880
ttcagaaatt agaggaatca cgattgaccc cgtataccgg caagaacttc aagccatgta   26940
cgctatttat aaggatagca aggataacaa gcagttcact gaaaagatgg cacaagctgg   27000
atatggaaaa ctaaactaaa aggagagcca ctatcatgaa actatataag ttgttaatcg   27060
ctattgccgc aagcgtcaca ctgtcactag ttaccgcata taatgcggac gctagtcaac   27120
ggcctaacta tgcgtataca ttaacccgta ctaaacagca cgcagttaag cttaccaata   27180
ccggcaagac tgaaaacttg tatcgtatca ctgttaagcg tggacgcgcc acaacgtggt   27240
attatatggc tttgaatgct aaacaatcat ggacggtcaa ccagtccgga aagtatagcg   27300
taactgttcg gcgtatttca aaagcggatg aaaaacgcaa tgcagaccca cggaatcatt   27360
ttacgccaca aggaattaaa aacacccagc aaactattta taaccgatag cataaaagaa   27420
ctagcattaa gctagttctt tttgtttata ataatttaat catatatgca agcctaatta   27480
tatcgggtag ccttaaaatt gcttaaacgt ccttatgcaa gcatttaaac gcatatgaaa   27540
ttattttaga tagccccttg acaactgtat attattttttg ctatacttta tattgttatc   27600
aagtaaggat aaaaaagata tttcacgtta aacatttaaa attaatcctt gacgaggtat   27660
tcaattagga ttacaattaa gacattaaat agaaagaggt tttacattat ggatattaaa   27720
gaaatatata atcaacgtga ggagctacaa ctaattgtaa atagggcaag caaccaatta   27780
aatacctatg attcaaaatt gagtggattg gtacccgata atattcgcga tacggaagaa   27840
tataagcgtg attataaaac ttataagcaa gctttcaacg acttgcaaga gtttaataaa   27900
aagctttctg gaacacaaaa aagagaatta agaaatataa acggcaact aaaatacagc   27960 ttaaattaat ttataaatag tcttgacaaa ctatcacatt aggtttagaa ttaggtcatt   28020
caattgaaag gggctgacat attatgacag caaacaaaaa gtttcaaaaa ttagtaaata   28080
acggtgaatt aacggacgaa caacaggagt tagcttatca atatgggggtt attgacgtaa   28140
```

```
atagtttata cgaatattta actgacaccc tagccagcga aagctttgaa gatagcgggc   28200
gtgtaattga actattaagt gaattactcg aatacgattc taacgattat gtattgtatg   28260
atgatgacaa aatcagcgaa ttagattatg atacgattga agatatttta aattagtggt   28320
gtataaaaat gaaaacaatt aaattaatta tggttatcgc aattagtttt gtaggaacaa   28380
tcgcactact tacaacgagt gcaaaagcgt tcagtattac cggagtacaa ttaacaaggg   28440
ttaatcatga gaattacacc aatatcgcga ttactaaccc tactcataag gatagggaat   28500
atcatgttat cgtaaagcca gccggccaaa aggcgcttaa acttaacacg tatattcaag   28560
ctggtgaaac tgttgagata tatacgccag tacgacataa cggtggtatt ctatacaaca   28620
agaaactacc taaaaaattt accgtaacag tatatcgtat gagtagcaag caaagtaaat   28680
atgaaatgag acacggatat gttaacgcgg gtattaaatg gactaagcat acattaacta   28740
ataagtagta attaaagtcg cttaatgcga cttttttatt ttatttaaaa taagggttgc   28800
aattaagcgc cggtcatggt atattataaa catagaaaag aaaaggggggt tataacaatg   28860
aatgaaacaa ttaaggacgc attaagtaat ataacgcggt atgatgatat tgaggactat   28920
ggtaaatata acgtggcgc aacaatggac gacttacaaa aatatattaa tacaggcttt   28980
gttgctgagt taacgccggg aacttataac ggtgcactcg ataagtttga ccgtgttact   29040
aaattaaccg acaacgatat tattaacgcc attaagtcgg aactattgga agatggtttc   29100
ataatcgaga cactagaaaa ttattacccg gaggataata cgaccgacat gcaagtgcta   29160
gactatacag acatttataa tgtgtttaca atcggggaac gattatacgt tgatatggat   29220
taagatacac cgagttataa aaagttaagc cacacaatta cagcacccttt aaataagggg   29280
tgctgttttt tgtgtggtct tttaatgtgt ggcttgtgtg atggtgtgtg tatgtgtgtt   29340
tatataagcg tgtgagacag gttgcaacat gacaggtata actatactgt agtgcattgg   29400
tattcgttac acagcttgct aggtgcattg tattggatta gtactaataa gatatgtggt   29460
tgagcaatga cgttagatat ataactgata tagttgtgta tgatgatgtg tagttgtgtg   29520
tgtgataagt cttatatagt tgtgtgtagt tgtagctgtt gtgtatacaa tgcgttagac   29580
gtgcttacat tgcgtgctgt gaagtgtgta tattaatgta gtagttaagt gataagttag   29640
tgacatgttg acaggcgtta tataagacaa ggtacacatg tgattgtatg tagttatgtg   29700
tagtgagttg ttgtgtgttg tgtatgttta gttgttgatt gatattagtt agttgattgt   29760
gttgtgattg attgatgttg tgttgtgtta gttgtgttgt tgtgtgttga tacattgatg   29820
atgttgttga ttgatgattg attgatgttg ttatgttgat gttgtattga tgtgttatgt   29880
gattggttat gtgagtggta acgaatgcag tcacgaatcg caatgcaaac ggattgaatt   29940
cgcttaatga tttatcaatg taattgattg gaatgcttta atagttgaga taaaaattga   30000
tatagtttaa taaaatttat gtgtttaatc atacatttaa acttacaaca ttagattatt   30060
gttgattgaa ttaagttgat tgtgttaatt gttattgatt gtaacgtttt tagtggcttg   30120
cataccgagc ctagccgtgc acccacgcac gtacggcacc ccctgaacaa actcagaaaa   30180
aagaaaaagc ttaaaacaat gagcgcccta cccttaaaca cacaaaatcc tggttcagaa   30240
aaaatagggt tatctttttt gaccgttta gggcgcactt atccatcttt caaacttcct   30300
ttctttgatt gtctaaatca tatcacgtta tcaaaaataa tgcaacactt tttattaaaa   30360
aaagtcaccg attggtgact aatgttccta acatattaat tactcaattt aacgttcatg   30420
tcaacgtcaa ccttaacgag ttcaacgtgc tgtgcaaaat agtgtgttac catttcagcc   30480
aatgtatcaa acattggttc tgccgccaaa actggatgtt caccaactgg aattaaaaca   30540
```

```
tatttcttcg tactatcatc aattgcgata ctcgttacat gataaacgtg attatcgtca   30600
actcggccat tcataactct cattaaccag tcgcctacct tgtattcttc tgttgctttg   30660
attgtattat caaaattaat tgttgtcatt attataccct cctaaatttg cgtctgttct   30720
tctgcacgtt ccaacgcgac atctaataac tcatggaccg aactattctc taattctaac   30780
ttatgtgact gcgaaactaa tgccatcatc aacaacgccc aagccgcttc atcactcatg   30840
tcagaaccaa acttcaattc accatcgctg atactagcta caagcactcc atctaaatta   30900
tccattaata tttccttctt tcaattaata tagttgtttt acaatattaa taatatcaaa   30960
aaacttatct gtataaccca cccatggaat cttagttccc atggttaaat caattacctt   31020
atcttcaaac tctttgtcaa aattcggtag cacattttg aacgcaattc tgaaacaatt    31080
ttctagcacg ttactattaa attctcgaat cgctcctacg ccgttattgt taataccgtc   31140
aagaatatat tcaattccag acaatacttc acgttcgcta tcgcctccat tgtttctttc   31200
cgtaatatac attttccctg caaaatcttt ggcgtcagta ctctctaata aaaacttata   31260
gtattcatca ttgttcatat cttatccctc acttttaagc ttggcccatc attaattgac   31320
caatatatat tatcgcgtat acaaatattg caattgccgc taatatcaag atggtcaata   31380
taacgttgta aattatgttg ttatctaata taaactgaca taccttagtt cgttcaatca   31440
ttgatattgc aaacattacc aatccgattg cgactaatat caaaaacata gtcataaatc   31500
ctacacaaaa gctaataaat atattcatta tgttcaccta aaacgttacc aagtatgttc   31560
ctttcaatag gcggtcatta ttttcgtcat atgaatgact aattaaactt tctttgtctt   31620
tggacgttac gcaaaccatt ccgctctcta ggtcaattaa tgaatattca gcggttacta   31680
aataataatt accatgagat acaatcacat tgccgggttc atacatgtcg cttgcagttt   31740 ctacttttc attaatcttc atattttcct cctaatggat tactatcgta ttatcattga    31800
cataattgaa tttatcaatt gaaaagcgtt caaagaactc attaagttcc attaacccgt   31860
aaattaattt tccagtggtt aaatcaacca agccataaaa aagacattct tcacctttct   31920
tagagattac aagacatgtc ttgccgtcat agctaacaac atttccggat tgtaatactt   31980
ctccttctgt cggcttcggc ttcttgtaca ttatcttcat ttaatatcat ctccaatacc   32040
attagcttca atgtaggcgt ctagcaattc tgttaacatg tctacggatt cttgatagtc   32100
atagtcacaa acatcaagaa ttagatgtat taacggtgag ccaacggcat ttaaaacgtc   32160
tgctacattt aaatcatcgt cagattcaat caccttcata cggttcccat cttcgttagt   32220
ttcaattaaa attttaatca ttatacatcc tcctatttaa tcttcatagc ttttagcgc    32280 taaatttgca aattcaaaag ctgttaattt aacatcgttg ttctgattct cttcttttac   32340
aatctttgcg gccgaatgta acaataatgc aattgtcata gcttggtcga aatcgctatc   32400
tacgtacacc gaaccattat caaccctaac ttgaatttta ccatttttcca ttttatatt   32460 ccctcctaat taagacactc gtttgcatac ttctacgatt gcacctagaa aaattgaaat   32520
cggaattaag acatgggggt acacagatat tcccataatt ataattccaa ataccgctaa   32580
gcatatcaac ccagcgataa ccgacaccat tagatgaaaa aatccatgca caaacatatt   32640
tattcccctt ttctatttaa ctcctagtag ttttacaagt ctatcaattt cttcttttgt   32700
taaattgtag ctatcttcat tagttaatcg tacttcacga agaatgctgt tgatactaag   32760
gatatactgt aaattaatgt atactcctga tgattgtaga aagaacatta ttatcacctc   32820
gctttcaata tatgtatgat accaccaaat taggcggtat gtcaaatgtt tatttgacca   32880
```

```
tatttcgtaa atcaaattct ggaatttcag ttaacgattc tttgtaactt ggcaagtcta   32940
ggataacttt aatattaata ggtttatctt tgacggcttt ttggcttctc ttaatgtaac   33000
cataatgtcc catgtaatcg gcaaattctt tgcggtttag tcggcgtgta tggtaatcaa   33060
aatgattgtt ttcgcagaaa cgtgcataag cactgaataa cccctttaaa cttacattca   33120
catcatgagt tttaggcaat aaatccagtg atgtccaatc ccagtattca tcgagaaatg   33180
aacataagat ttcacgttta gtcaaatcct ttttgcgtga atgaccaacg aaccgactat   33240
caatactatc aaggaaatca gactcttcgt tagtaatccc tttaccatgc cgaatatcgt   33300
acaagatatg ggacagagta ttagcgtcct tagaataagg agcaagcata ttgtattcta   33360
ggatggcgtc tgttgtttcc aacttttgaa tcacactggc gtcatagtcc attaacccat   33420
caccattata cccttgaact atgcgctctt cgtcaaaatc ttttttacca cttaacatct   33480
taaattcctt cttccttttta ttttgtgatt atattgtatc atcatttttt cattccgtca   33540
acattcttat attttgtca aaaatcaaga atgccgtcat atcaatattt atcaccacac   33600
aaaaaacttt ttatattata gtttgatgag atagttattt attggagaat atcggtgttt   33660
ttttctctaa taaagtctg atttatcgtt tattgaagtt agcctagggg tgaggaacga   33720
caacagcttg cctgttggcg tgacggtgag gggtgtcgcc gggtgtgggt gaaacccacg   33780
ttaacgtgat tataatgggt gaaactagga gttacgaacg tagtgagcta ctcctagtta   33840
gcgctttagc gcttatccct ataaaggaat agtagagcat ttaagcatat ttaagacata   33900
taaaacgaag cacataacaa aaggtagttt ccgcactgta aaaaaataaa aattttttta   33960
gtgtaagttg ttatttggag aaaaaaacac ttgttttctc caataaaagt ctgatttatc   34020
gtttattgaa agcacatggt ttaaacaatc aatcgactta caaggaggt ccgcttaatg    34080 ccagttgatg acaaattaga actcatcaaa gccattctat atgcaagcga tgatattaac   34140
acagaagata aattaaacgc agtacggtac ttagtctatg gttgggatag tgagtcagag   34200
gttggtgcta aatcttatca accatcatgg cttaatgatt tatccattga aaccagagac   34260
gtggttaatg gtctatcaag taactaatgt tccattaata tattcaactc actaattcat   34320
tcattattat actttcctcc gtgggagatt aatttctccc attacatata ctaggcaatg   34380
tggcgaataa ttgaatatta ttcaaaaact acagttcagt gcactaactg gaacgtcctg   34440
aatgtttcct acgtctttct tatcaggaca ttacatataa aaagggagga cttagcatga   34500
caaaagattg tccgtcatgt tcaactccag ttgagataaa caagaaagat gattatgtca   34560
tttgtcctta ctgtggcaat ttgcttgaag tggacggtga tgaccttgaa gaatacacaa   34620
tcgggtagag atttatctgt gtgcccttat tgtggaatga ttgtagagat aagctctcat   34680
gattgtcctg taaaaaggaa aagagataat cataatgcaa gggtcgcacg tcaaaatcaa   34740
acagtcacag agaaggcttt gacatctcaa aggtggcgtt ctttagaaa gaagattatt    34800 ctaagagatg gtggtgagtg tcagcgttgt ttaataaagc tacacaaaca cgtttatgat   34860
gacttgaccg tacaccatat acagccacgt gtcaagcacc cagagctaat gtatgacgaa   34920
tcaaattgtg ttacgctttg tcgtgaatgc aacttagcta tgggtctaaa cggtatagat   34980
ttcgactggg atttaacaaa gacaaaaata aatttagatg atacgcttca tttctaaggg   35040
ggtgaacaca tgcctaacgc tagaaagcct gcggcgctag ttaaaggtca caacgaatcg   35100
gcttctgctt taagaaaaag aatggaagac gaggagcgac taaaaggtgc taacgacgag   35160
gtacgtgtgg cacctgattt tatcaaaggg tgggaaccg ccgaaaaata ttatgactat   35220
atttgtgact tattagaaaa ttcagatatt ttgtctaact tagatagaat gggtgtcggg   35280
```

```
gcacttgctg aatgtctcgc tcgtatggaa gaatcaaata aagcgatggc agatgatggt   35340
ggcaaccttg tgattaccgt tgaaactaag aacggatata agacggttga aaatccttat   35400
attaagacac accttaaatt ctttgacagg tttagggtgc tgtcaacaca gtacggtcta   35460
tcaccatcaa gtcgggcaca gctaagtgcg ttaaccattg aagatagaag taagggtaat   35520
agcgcacttg aaagtattat taacagtgac gattgaagat attacttcct agtcttgatt   35580
agactaggct acataattag ctcaaagagc aatacagcga ggtagttcaa ctcgcttatg   35640
ttacatagac gggatatagg acagcttggt agttcactcg gtttggaacc gagatgtcgt   35700
tggttcgaat ccagctatcc cgataataag ctcagtggt gtaatttggc aggcacgcaa    35760
gatttagaat cttgtgtcgt aagacgtgta ggttcgagtc ctacctagag cataatgttt   35820
attataggag gatataataa tatgaatgaa ttaacaccga atgaaaaggt tattagcaac   35880
ttaaaagcag aacgagcagt agttttttcgg gatgttaaaa aattggacga gaccatcagc  35940
gcgggtaact cttttattag tgaagaccaa ttattctata tgaagaagca gtcttccgct   36000
atgaaagaat acgttgtctc gttagatagc agaattgaca atcttgaacg ccgcgaagcc   36060
tatgaacata agatgacgag taaggaattt attgaacgga gtaagaaaat cgtttacgac   36120
cacatcgtca acttatatgg caaagattat atcaaagtct ctgatatta cgttgtctgg    36180 tacgctaggg aattacagaa tgataaggct ctattaagca ccaatgtttc agacggtatg   36240
tattatgagc taactcatga tggcgataag cgcaaaattt attttgacgc ttataagaag   36300
actatcaatg aaagtcacga ggaattttag tgaatattgt acagaaagtg cttgtggcgg   36360
aataggtaga cgctatcctg agctaaggtt gaaagaagcc aggaacggat aggagagtac   36420
aaaatccagt atatgtaggg tgcaaatccc taccaagcac attacagtga gcgactgatg   36480
acgtgtacgt caaaaaaacg ttagttacca ttaaactaaa aatggaagtc gacgtgtggt   36540
tgaagcatgg ctagataagt ccccacgaag ggccgcccat gtcaggaggt tagctaccgc   36600
gtgtggttcg attccacacc aatcacgtta agttaaacgc gcctgcgtct cataaacggg   36660
caatatcaac agcacctagt acacctccta acagtgtggc ccaagctagg actttatcag   36720
agtaagctta actggcaaac tgccggactc caaatccgga cttctaggtt cgaatcctag   36780 cttgatgtg tgtgtttttt attaacgctc ccctagtgta attggttaac acgctaggtt    36840
tccaacctag taatgtcggt tcaagtccgg ccgggagctt gtagcttaat tacaataaag   36900
taaaacgttt cttggtgttt tcttttccatg ttcttttaaa ccaagagtac ataaaatgta   36960
gattttacag tctatattat agcatataac gaggtgatat gttgaaaaat aaagatattt   37020
tcaaccaccc agcgtatcaa tatgctctca atgttcataa tggggaaact ctggctaata   37080
aagatgttaa aatcgttgcc gatagattta tcaaagaggt tgatgatagt cttaatggca   37140
agggcgacta ctattttgat attaacgcac ttaatcgtgt ttctaaacta ttaaaattaa   37200
ttattatggc aactggccca cgtcgtggtc agagtgcata tgactcactg gctggttttc   37260
aatggttttt ctttgtcaat atcttttgtt ggcgtcataa agagaaccat aaattgagaa   37320
gataccaaac ggcaacaatg ttaataccta gaaagaacgg taagaccttt atttcggctg   37380
ttattttcat tttgttgctt attttagagc caaaatattc gaaattttac tctgtagcac   37440
cagatttaga gctatcttca atgttgaaga cgcaaatcga ctcactgatt gacggttcac   37500
ctgaattagc tcggtttttt aaggttaata ataaggatat tacgtgttta ttgactaaaa   37560
atagttacaa accactagct aacagtaata atcgtcttga cgcacgtgaa ccagtggcgt   37620
```

```
ttttggccga tgaagttgga gctttgccta atagctatcc aattaacgcc atgaagtctg    37680
gtcaaacgtt ggttgataac ccattgggta ttatcatttc aactgcgtat gattctcttg    37740
ataatccaat gacacaggaa attcaacgtg ccactgataa gattaaagac ggagaattgt    37800
atgacccgac gtattttgcg ttgatttata ggccagataa gcctaaagag tgggctacaa    37860
acgatgaaga gctgataaaa gtcaacccac tatcgcaaga aataccaaga gttaaagagc    37920
gcttattaaa cgagcgagaa gacgccgtta attatgaaga taagcgtcaa aacttcttaa    37980
caaagtacat gaatatcttc gttgatggtg atgaaggtga gcaatttacg actgaaagtg    38040
agcttgacag agctgaatta ccacaaggac ttgattggta tggtcgtgac gtattcgtcg    38100
gacttgactt tgctgaaagt catgataact ttggtctagc catggttact ttcgatgaag    38160
aacaccagaa atatgtcgcc aaggcatggt cattcttccc agcagaccga gtcgttgcta    38220
aaacaaaggt tgaaggctgg gattaccaac actctgaaaa cgagggttgg ggattttctt    38280
ctggtcatga acaattgat  tatggttttg tagaagattt cttctatgac atcgaatcaa    38340
agtacggggt taagattaaa ggattcggtt atgataagtg gaatgcacgt tctacggttg    38400
ccaagtttat cactagtggc tacgatggtg ttgaaattcc acagaatcca cgcgggttgt    38460
atccgggcac aaagcttctg cgtgaagcgt tgcagaatgg taatttcgct tacgataaga    38520
atgatatgct acgtcagaac ttcttaaatg ctaagatggt tactgatagt aacttatcat    38580
actttttaaa caagaaaaaa tcaagcggca agattgatat ggccgccgca gttgttgacg    38640
ccatgtcgtt atgggaaatc gaagaatttt caaacattat gggtggcgca agcaacatca    38700
cattacttta aaagggtga gtttaaatcg ctaataagaa taataaatgg tctttaaaga    38760
atatctttaa aattccgttt agccagcaac agccgggaca agacagtcgt ggcggtactt    38820
ttgttcgttc acagactggt acagggccgt tatctttcac tggtgacgat acacctatca    38880
cagaagatac agttatggag attccggcgt tcagtgcggc gttagcgttg gttgctgaca    38940
cggtagcttc tctcgacatt tgttgatga agacaagtga ccaaggtgtc ccacttcctg    39000
ttaaagatga cgaacgagta ttaatgctta ataagcaagc aaacgaagag atgtctgcct    39060
ttacgtataa gcgttcagtt gttaaagact tattattata tggtcgttcg ctaacttaca    39120
ttgaacgaac tggaaacaac aagattaatg ctatttatcc tttagcttct cgttatatca    39180
ctaccgaagt ttatacctat ggtggctata aatactatgg tgtttatact tataattcag    39240
aagctggttc atttgagtac gatgaagaag atttgatgaa tgtgatttct gattcgcaag    39300
acggtatcac agcagatggt attatggcta attcactgg  aacacttcaa ttagctttag    39360
cgcaacgtga ctacgagaaa aatctgttgt ctaacggtgc ggttcccgtc ggtgctgtac    39420
gttctgacag agcagtagcg ccagaaatcc ttgataaatt gaaggaacag tttgctaaat    39480
cttattctgg tgcaggcaac tctggtaaaa cgctattcct agaaggtggc ttatcttacc    39540
aacagattag tacaaaccca gataatatgc aactggattc aagtaaaaaa agcatgttag    39600
gtgaaatcgc tcgtatgttt aacctaccgg aaacgcttat taacgctagt gctaataagt    39660
ataattctaa cgagcaaaat aacttgcaat tcttccaata ttgtttaaaa ccaatttat    39720 caagttttga agccgcaatc aacaaggaat tgttattgga atctgaaaaa gacgaaggct    39780
acttcttcaa gtttgataca gataccatta tgcaaaacac ctttaaagaa aaggtcgccg    39840
catacggtgc tttatacaag cagggactta ttagttatga tgaatttcgt aacaagtttg    39900
gctttagtaa tattgaaggt gaagacttta ttaaccttag tctcggctct gtgctttatt    39960
atcctaagac tggtgaaatg aagattccta acttgggtat cgctggaggt gctgacgttg    40020
```

```
ccggacagga ttcagatgac cctacacagg ttactcctaa gaatcagcca attggtacca   40080
tcaccccaaa taagaagccg ggagaaaaac aaggtattca aaaagctcct aaccaaaaga   40140
atcaagatga cagccatcaa acaaaggctg ataacaatgt gttaggaggt aatgacaatt   40200
aagcaaaaag aattacggac acttagtttt gaaacgcgag acttatcttt tgacgataaa   40260
tctttaaagg tatctggata tgttaacaaa gctggctctt atagtcaagt gatgtctgct   40320
gacggtacac cgttccgcga aactattttg ccgcaagcat tgtcgaagc tgttgcaaca    40380 gaagacccaa ttgattttta tgcagaacat gatgaccaaa aattactcgc aacaaccgtc   40440
aatcattcat taatgctacg cgcagacgat aacggcctgt atatgaaagc acaaatctta   40500
gacacgaacg atggtcgtga tacctatgag cttatcaaga gtggggttat cacaagtatg   40560
agttttggat ttattgttct tgacgatgat tgggatatga ctggtggcaa ttttgatgat   40620
ggaattccac taagaactgt caaagaaatt attctgaaag aagtatctgc ggtacgtttt   40680
cctgcttatc taagttcgag tattgaagct cgtggtattc aggagttaaa acagcttgaa   40740 catagggggta ttaatagcgt atcggaagtt gttaatatta aggagggaaa cgaattggaa   40800
ctacgagatg tagaaactaa agaattattt gctgaattag aacggcgtgc aaagcttcct   40860
gcaaacgaag ttattgtaaa accggctaaa cgagatgatg aaccagatac cactgaacca   40920
caggtagctt ctggcgtagc cggaactgtt gacgctttat ctccagtaaa tcaaattgat   40980
gttgatgagc tgtctaagca gattgttgct tctgtcttag ctggtattca aacatcatta   41040
gctcaacgcg atggagaaga agatgttcct gaaccagatg gttctgacat ggcaacagat   41100
gatgacactc aaactgattc aatgaaaacca gcaaagagtg caaaatctga tgaaaagcgt   41160
gatgatgaac ctgatgattc cgatgaacca gacgatggct ctggcgatga aacagaaacc   41220
gattctaaga atagcaagaa ggattctaag agcgctgaaa agcgtagcat ggaagcgcgg   41280
gaattattga aacaaattaa tgatttggag gtctaattaa tgaagacaaa gaaaggtttg   41340
cttgaaaagc gttctgcatt aaaaggcaag ctagacgcta tcaagcctgc tatcgaaggt   41400
ggaaccatta ctgacgaaca attggaagaa atgcgctcta ttaaatcaga tattgtatca   41460
gttaacgaag aaatcgcaaa tttagatgaa caacggcata acgccgtacc tacaaaagat   41520
gaaactaggg gtgctgaaaa aatggataaa gacttaaaga aactcgaaaa gcgtgcggcc   41580
gctgacctat tccgtaacaa gttgcgggat agcaaggcag ttcatgacta ccttgaagtt   41640
gcgaaggaac acgacaagga cgttgacgta gaagaccgtg cattacaaga taacggttta   41700
tcatggggta atgccgtaaa tggtactgct tctgatggtg gtgttgttgt tcccaccact   41760
gttgccgata ctatcattga aaaactacaa gaaacttctc cagtatttgc attggctaac   41820
aagattggtt caatcaatgg taacttgcgg gtggctcgcg aaactgataa ctctgacgat   41880
ggtttcgttg gtgaacttga agaagttaag gcacaaacgc caacgttgaa atacgttgaa   41940
ttaacgcaaa agcgtgtcgg tgcttcaatg caattatcaa acatgatgat taatgatggt   42000
gcgcctgaca ttgttagtta cgccgttggc cgtttgggtc gttcattagc taaagccatt   42060
gaacgtgccg tattaattgg tgctaaaact ggtgaggacg ctacgaagac cttcaagcca   42120
gttgttggtg gtgacggtgt tcaaacgatt actttggccg gtgcaactcc tacgttagac   42180
gaattgattg gtttaacgac tgcacttaac cctgcatact ggggcaagc agtgtttatt    42240 atgtctcgtg aagctttcaa cgctgtatct aagttgaagg acgatgacaa cgaacactta   42300
atctttaagc cacaaatgca aaccgctatc gcaggtgctg ttggcgttcg ccccggatat   42360
```

```
tcattccaag gtattcctgt attcgtatct gaccaactca acggcaacga aagcggtcaa    42420
atcgtattag gtaacttcaa tgcagggtac accattatga ctaagcaagg cttacggtta    42480
actcacgtta ctgctgatac tgctcaagca ttggctggtg gtcatttaat cgttcttgat    42540
ggttacatgg acggtgctgt tacgaaccct gacgcattcg tagtcgctaa gcctgcgagt    42600
aagtaacccg gcaccaacgg tcactagcgt taccoctaac gtgaatagcg ctacggtggt    42660
agctaagtaa taaacccgat tattaaacct cctcatttga ggaggggtac atatatatag    42720
gataggaggg aatgctattg gcacaaaact ttgatatttta cgatgataaa gatgaaaaga    42780
ttgtaaccaa tcaaccatct ccagttgtaa tttcagacct caacccagcc actaagtatt    42840
ctggttataa gattgcttat actggtaagg attcaaagac aacgattgat gattttacga    42900
ccaccaatca agtacccggc aagccaacgt tgatggttag tgccggtgac ggcaaactca    42960
atgttatctt ttctgacggc gaaaatcttg gtacggtagt tactaagcgt accgtctatt    43020
ggaagtcagc agatggtaag accggcaccg ctgactttgg tatgtcgtcc agtggttcag    43080
ttgacaacct gacaaatggt acggaatata cactacaagg tgtatgtaca aatgccgctg    43140
gtgactctga aaagtcagac gaagcaaagg ggacgccagt tgcggctgga taatcccacc    43200
ccaattttgg ggtacatagg aggtgtaata gatgtcggtg acgattaacg attttaaaaa    43260
tcaaattaat gcggattcag atgaagatgt tgatttatat tttaaccatg ctgtcgacta    43320
tgttaatttt tatgtatcaa aaattgctgg tcagttcacc ggtgaccgcg agaagcaatt    43380
cgagtcaacc attgatagag cagtattaga ggtagcgaca actctttatt taaaacgtga    43440
tggtgcacct gttagcggca ctattaattc ctcctcacta gaaaccatta tcaattatgg    43500
caggaatttt tccatttagt gagtgaggtg agaagatggc aaataaggtt gacctatggc    43560
gctacaagga aaagttagag cttggcacaa acgaatcatg gaaagagcta gacaacggta    43620
acattatcaa ctctggagct gacattaatg acgatacatt tgatgttaag tatacttttc    43680
attgcgcgca atatcgggta tcagatagaa atattacgag tgttaacgga atggacgacg    43740
aaaatacact cgtagtcgcc gttaaacaca gaccgaactt tgattacgat agttaccggg    43800
caagattcag aaagaaatat ttcattgtaa cctatattgt accagatact gccgcaattg    43860
tatcatatga tttattatcg ttgaaatcag ttattaagaa cggtggttca tctggtgtat    43920
ctggcatttc caattatgga gggggcgatt catatggcga ttaacaagaa attggttact    43980
aatagtttag gctcaattga ggtgactggt gaagacgagt tacttaaaca gctagacaaa    44040
tttaaattat ctcgtaagga acgttcagct attgttgaag ccgctattcc aattgctgaa    44100
aagcacctat atgatagcac accttatgat gaatttgaag acgttcacaa caagaaatta    44160
tatggtaagt caattggtca tttaagagac catattacac ataagccaaa ccaatttatt    44220
gatggtggta ctgaattagg atttgaacaa aaagcatatc ctatcgctgt ctggactgac    44280
tggggaacat atcgtcaacc ggcacagttc tggtttgaga agtctgttga gactatgccg    44340
tatgaccaaa tctttgccgc tcaaactcaa acagctaaag ctatttaa ggcaaagggg    44400 ttgtaggatt tgatttcaaa cgatgttaaa caattgatta gagacgctaa tattgatgga    44460
attgacccaa aatacgtctt tgcgtatgct cttcctgata atattaaagc ggcagttcag    44520
aataaaatag tgattttagt taacgacatt tcacgtattc ctagtaagtt tgggagcgat    44580
gaaatcatcg ctgacgacgg tacggtacaa gtgcagttct tttatccgtt aagtattgga    44640
ggagatgtta cagcgctgta tgaacaccct gtacgtaaca tgttacgtga taatggctgg    44700
taccaaacaa ttggtggtgg aattgaccgc gaaccaaata catcacaact ttattcaact    44760
```

```
tatcatttca agaaaaccat ttattaaaga aagaggtaat tactaatggc aaaaaccaaa    44820
ggtattgaca gcgcccagct tgctatcttt aagcaagacg ccgaaacggt tgacctaaca    44880
aataaggcaa tcggggcaac gggtgtttat aaattagacg aaaagaccgc gcaaggtatg    44940
acggtcggta acatcactgg tcttgcacca acgatgacta agatttacgg ttctgacatg    45000
gtcgttgaaa cttctggtaa gggtgttggt tctgtccaag caactgttgg tgccaacgat    45060
attccagaag acgttattga cgccattact ggtgttgaca acactaaagg attttctgtt    45120
gttacgtcag atacgcgtgc tccatattca gttattgaat tcgttacgca cggtcgctta    45180
aacaacattt tgcattttgc tttactgaaa ggtacttttg gtcttgaaga acacaacatg    45240
caaacgaaca ccgaatcaga acaattagca ccagactcat tgacgttcac tggtgttaac    45300
cgtcaagctg acaaggccgc ttatgctaaa ggtgacgaag ctaacgacac gtttaagctt    45360
gaagattggg agaagtttat ctttcccggg tacactccca gcggaaccgg cgcctaaggt    45420
cgcgtcgata accccaagtg tacgcagtgc tactattgtg gcagaatagt ctctatgcgc    45480
cccattaagg ggtgtgtcta catatccata aaataaaata tttagatgaa agacgaggag    45540
attcacatga ctgtcaaaat caatgcaaaa gatttaggaa ttcgtaagcc cgttgaagta    45600
aacgagacta acaagaatat taagaaaaca ttaaaggtgc aaatgaagtt ggaagcgtta    45660
ggtaatattg acgctgaaaa catgaccgat gaagaagcat acagtttgtt cattaagaat    45720
caatatgaag caaacgaagc aactaccgaa tatattgctg accttctacg tttatcagaa    45780
tcgcaagttg ataaattaga agacttagaa tcaagcaaga ctgacgagtt gtttgctcaa    45840
atcgttcaaa agattatgca cattgaccag attgcggacg gtgacgaaga cgacggtacg    45900
cccagcagaa ccacagacgt ttcaggagac actggacgag attaatcgtc tcgaaaagac    45960
actgattgct caaaagcaag atacgtttaa caatttagag gaaactaact attttgattt    46020
attagaaact ctatctgtcg atgatgacga tagtagttct ggttccgatg atgaagtagt    46080
acctctaggt tactggttgg aagataacat tgccgagggg tagtgttatt gtttacttat    46140
ttttgttggt taagttcgct ttggcgggct tgttttttttt gcaaggaggg ttttaaatga    46200
aacaggccgc atatggtagt ttaacataca atgttaacat taacgatacc aaagctcaat    46260
cgagtttgcg tacgttaaaa ggagccattc gttccacagg ccaagaatgg cgttctaacg    46320
cttctgcaat gcaagccgcc ggtgatagtg caagtgcttt agacgctaag ataacaggtc    46380
ttaataaaga aattgagcta caaactgatt acaataaacg tttagcagaa gcattgaaaa    46440
atgcgaacgc tacaactgac aaggaaaaac ttgcagttat gcgttggacg aacgaattaa    46500
ccagaagtaa cgcggcactt aaacgtcgtc aaagcgaact agatagcgcg cgcgcagccg    46560
aaatcagata ctcaactggt atcgacagag cacaaaagtc acatagagct tataccaatg    46620
cgattgaagc cagtgaaaag gctttgtcag cagaaggtaa agaagaacaa gcaagtgcca    46680
agcacaagga actcttagcg gccaagacat cttcattgaa agacgagctt ggacgtgaag    46740
aaaaggcact taaagcgtta aaggcaagcg ctagttcttc taatgttgat attaacaagc    46800
aatccgctgt tgtatcaaaa gctcgtgaag cctatgctaa agctcgtgaa gaacagcgta    46860
agtattctac tggcttacat caaatggagc agtattctaa atcaactgct gaaatatcac    46920
aatcacttgt ttcaagattg cgagcagaag gtaaaaacta tactgcaatg tcagtagaat    46980
taaagacctt aatcggttct cgtaaggggt tattaactca atacaaaacc gaaatgtctg    47040
aactagagct gattaaaaag cgctctggtg acacaagtgc ggcttattca gcgcaagcta    47100
```

```
aaaaggtcaa tgacttaggt gcaaggattg gagaaacgga ctcaaaaatc cgttctttaa    47160
ataaaaatgt tggtttgtct ggttcagcaa taaactcatt tagtgataaa attggcggta    47220
tgcaaaagaa atatgcgggt gtcgctaatg caatgtctgc cgtttctcgt ggtactgggt    47280
acgcaacctt aggtcttgcc gccgtgacta agcaaggtgt ctcgatgtca acctcgctag    47340
aatcttcttt cactaagact aaaaacttaa ttgttaagtc taacacagaa ggaactagtg    47400
aaattaaccg caaccttgca agcatgaaag caaatgctca gtcatattct aaggaatatg    47460
gcttaacaca gcaaaagatt gctgacggtt atcaagattt gattaaacgt ggttatagtt    47520
cagcgcaagc attaggttcg atgaagacgt tagttaaagg tgctatcgcc actggtgatg    47580 atttttaacga tgtcacagcc gtttctacac agactttgga atcattcggt ttaagagcta    47640
```

```
aaggaattgg aaaattcttt gcaccagcta ttaaggcaat tcagacaccg tttgaaaaga    49560
ttggtaaatg gtttaagact agcccagtcg gtaagtcaat tgtaaccatt ggtaaagata    49620
ttgctggtgt agttaaaggt attggtaagt ttatcgcggc tttaggagca attgcaggta    49680
aattagccgc aattggacta gttaaattgt tccaaggaat cggaaaagct gttaaaaaca    49740
tgggtaaatt ctttactgat gttggcaaga agattagcgg ttgggcaaag agcgttcgta    49800
aaaccattga taatatggtt aagccaattc agaagacaat gaacaaaatt ggtagtggta    49860
tctctaaggc atggagtggt actctaaaga atgttacgaa gttcgtcaag aacatttata    49920
acactgctac taaatggatt ggtaagatgt tatctccatt ggctaaagct tggcaatcca    49980
tttctaaaac tgccgctaaa tggtggaaga gtatatctaa caccgttggt agctgggcgc    50040
ataagcttta taaggaggta actaagtggg tcggaaactt gcttagcccc gtagctaaag    50100
cttggcagtc tatctctaag acggcggcac gttggtggaa atcaatttcc aattcaattg    50160
gtagttgggt acacaaaatc tatactaatg taactaaatg gttcagaaac ttgttgtcac    50220
cagttgctaa ggcatggaag aatatatcta acactatcgg tggctggatt aagggtattt    50280
ggaagaatat ttctaagttc ggcgataata tggcaagctt cttcaagaag cttccgggac    50340
gcattgctag tgctctacga ggagcatggc atggtatttg aactcaatg gctggtatta    50400 ttaacaacgg tgtcattcac cccgttatta atggttggaa tgctgttgca ggtgctatta    50460
atggcgttga aaagaagatt ggtgtcggta agagctttag gctcgataca gccagttatg    50520
gttcagctaa attaagcacc tacgctaagg ggactccggg tggcccagcg ctagtaaatg    50580
acgctaagtc gaaatactgg cgtgaagctt acaagcttcc agatggtcgc atgggcatgt    50640
tccctaataa gcgtaatatt atcgttaacc ttccaaaagg aacagaaatt gctaagggtg    50700
aggacgctag aatggttcag ccttaccttg agcacactgg tggtaaaatc ccagcattcg    50760
cttctgcgac tggttggtta gatggtgttg gtagtgcaat cggtggtgct gtgcacggtg    50820
tcggtaattg gttctctgga gttgaaacta agcttctaa gcttattgat aatttaggca    50880
agatgattaa atcacctgct aaatatctat ctgctatgat tgcttcacca ttaaacgcct    50940
tggcaaaagg cggtggcata gccgccaaag ctgttggtat gactggtgat attgttgtca    51000
actctcttac tagttggttc aagaagatgt taaaagcagg ccaagacgaa caacttgtcg    51060
gtaacgtcaa gcttggtggt agcgttgctt cacgtgctcg tgcgttagct aaagcattca    51120
agcaaggcta tcctgcttct aacaacggcg gtatcgctgg tatcttaggt aattggattc    51180
aagaatctaa cttgaaccct tccgctgtca acgctagtga ccatggtact ggtttgggggc    51240 aatggacgtt cactcgtgaa actggattaa gaaattggtt acgtaaacac ggttacgcat    51300
ggaactccgc cgctggtcaa attggctatg ccttgaatga acccggcgca aacggaatgc    51360
taaaggccgt attgagaatg acaaatccta ctgccgcggc tcaaaagttc tttgcaactt    51420
gggagtctgg cggtaacatg gacgcttctg gtggtgctcg tttgagcaac gcttctgctg    51480
tataccgcta cattaagggt atggagaatg gtggccttgt tgataaagct caaatgatta    51540
acattgcgga acataacaaa ccagaaatgg ttgtttcttt gaccaacaaa gacgccgcaa    51600
ttcgtcaatt gaagcaatca attagctacc ttgaaagtgg taacaccgcc actaacgtga    51660
atactcaaaa tacttcgtct gctgatagtc aagcaattga acaaattgca actgctatcc    51720
agcaaactaa cgcattattg caagctattc tgtcatcaag caatactcca aacgttgctt    51780
acgtcgcttc acaaagtgtt gtagacgctg ttgaggcgca aaagttagct aaggcaaggt    51840
```

```
acaataactt gattaactaa ctaatacgag gggcaatccc ctcgtgtaca taacgattga   51900
atgggaggta agaccattgg cactaaaaga agatgaattt agtctaggcg gccttaatag   51960
ccgcacggac ttacacgtta ttatgggaat ggtgctccca ccaattgcac cggcaatgtc   52020
agaattgtca accgatattc ctgctaaata tggtgttcac tttggcggta ttgattatac   52080
tactaaaaca attaatattc caattacaat catggcaccg cataattcac agtcatatat   52140
tgattacgca caaaccttag ctggtttgtt attaacagat gaaccagaca atgaccgaga   52200
aattccgctg gtctttggat ttcaacctga tttaacttat tggggacaca tcaccgcaat   52260
tgctgaccca caagtaacac aagaagggtc ttgggattcg acatctacga ttacatttgt   52320
tatgtctgac cctagagcaa ctttaccaca ggttgaagtt ggcttaaagc ccggattaaa   52380
tgttattacc gttgacggta cagcacaaac agagccagtt atccaaatca tcccccctaa   52440
agcactaaaa tacgttgggt atacacttaa tggcggtaat tatggtattg gcccagaaga   52500
cccattggag caagcgcaag ctgttcaaga gtgggaaaag gtgctagacg accctgttga   52560
aacaatggca atgtggtcaa acgacgcaag cgccattggc ggtctaattc ctcctaacgg   52620
tggtgactat actgtattcc aaggagaagc gatgattaat gacgctactt ctgccatgac   52680
agttaagcgt gaccccggtg gtgctaacca acagtttggc cctcatcaaa ctggttggta   52740
cggcccagct ttaagatata ctggtttgac gcaatctctt acagattggc gtttaagagc   52800
tggtattcat catggacggt atggcggtac tcataatgaa cgtgcgatgg gtgcagttca   52860
attccagtgg actgacacag gtggcaaggc aattggtaat ttctgtattg ttgaccccgg   52920
acaaaacggt cgtccacgct gtcgtttgca aatttgtcag ccgggttcgg ttctcgcccc   52980
cggtgatggt aaacaccgcg atttattaac tacgacaggg cctagcggag ctttcactaa   53040
caagaaagat acagcagtta aaattaaaac tggtactaag acagttaaaa agactgttaa   53100
gactagagct aagaatggta aggtaactaa gaaaaccatt aaccaaaagg ttaatactta   53160
cgttactgtc tggaatcgtc aagaatctgg cgctttgaca gatggttgga ttaagatgga   53220
tatgcaacat gtcggtcaga cgtggagctg gtctgttgtc caatataaca ctgataacgg   53280
ccaaccatac acaaatccaa acaagtattt aattactcac tcacaacagc caatcaatac   53340
tggcactaag tatcaaacac cattaggtgg atttggtatc atgttcctaa acattctat   53400 cacagaagat gataagaaga ttgattataa agcaccttat ctttcattga ctggtattga   53460
attatggaaa cataatgatg ttccagattc atcaacccca acatatatcg ctagttctgg   53520
ctctgaaatc gttatggatt cagaagcaca gcgaacgact attggtggac ggatttcata   53580
tccagtatgg tctactagtt atccaaaaatt aaagccgggt gtaaattcgc ttaatatggt   53640
tggtgaccta gaaggtgcaa agatggtgct aaagtatttg ccaagaaagc tttaatagaa   53700
gcaagggagc aatcccttgg tacataaata atgattagga ggtaatggaa tgtcattagg   53760
taatcaatac ctcattttgg attcacattt taataatgtt ggcctattga ctgttgatgg   53820
agctacaaga tttactaacg actccattac tatgcagtta gcagattcag accaacaaaa   53880
tacacaatac gacgatgata ttagcgttgg cagtgaggat agctacgaag gaaaaacaaa   53940
ccttaatgca caatcaaaaa aatacgacca cagtggcact gtaacagttc cacagggggca   54000 accagatagt gataaggtgg tatctggtaa ctatttagca taccacgatg attatcttaa   54060
tcgttggtat atcatgtaca tttattcaac ttccgaagaa tctacctcaa caacttctgt   54120
aaatactgtt gcatacgtat gtaatttagt tctaagagac ttagcattta caattccatt   54180
gcaatcaaca gttaaacaac agaatgtcga acaggttttt agcaaagttt tccaaaactc   54240
```

```
tggttggcaa gtagagtata acacaggaag tgcaaccttac gcagacacgg attcatttga   54300
tggtaaaaca aaaggaaccg tattactaca aaacgcatta caactatttg atgttgaaat   54360
tgacgcttat gttaaaatca atacgcaagg taaagttgta gataagatag tagaagtaac   54420
agacgagctg tcttctgata ttgtttacca agaagctatt tttggtgaga acattacaaa   54480
tatcaagcgt gttacggttg cggcacctat cactaaacta tatgcgtatg cgcaaacgg    54540 ttcaacgatg gctccaaaca acaatggtat gacttatatc gttgatgatg acgctaatca   54600
gctttataac tatgaaggct cactaaatgg aaaatcccta gaaggtgtta ttaccgccaa   54660
tcaaattagt gataatactg gtttaaagtc ttgggccaaa caaatgttga agctattcaa   54720 ccacccctaga acctattacg atgttaatgt cgctcccgga tttttaccac cattaggtgc   54780
cacaattcgt tttaaagatg agcatattac accggcatta gatgccactg gcgtgttat    54840 tcaaagaaca attagtttct catcaccgta ttcaagttct atcgcttttg gtgaattcgt   54900
aactgttcct gttgcgacac cacaatggct aacagattac cagtcagcat agctgacgc    54960 tgtagctaaa gctattaacg acgctactgc tatcactcca gtgttatcac acccagacgg   55020 tcttgattt gcgcaaggtg aatcatcaaa gcgcttatta ttaagtgcat gggttggtaa    55080 acaaatatc agcacgtata ttgatagcaa agggtttgct tggagacatg ttaacacaga    55140
cggctcaatt gaccctaatt gggaacaaac aggtgacatc attaatgtaa ctccatcttt   55200
gatgggtaat attagggctt atattgatgg tgattatata tcagaagacc ctgaattgtc   55260
aattaatcaa acaattacg ttaagattgg tgaatttgac ccatatgata gcgacgttca    55320
ccgtattgca caacaccttg aacaattaga cgatggcact tggtacgagt cagccgctac   55380
ttctggtgat gattgcaatt atatgcaccg cgataaagac tttaagctta ttgataaaat   55440
ggttttaaaa ggtggaggac atggtacttc atttggtgtt ctgtatcaag agggacaacc   55500
atggattatc tgcaatcaaa gaaatagtgc tggtaattgg gatattgtta ggttcaagta   55560
tcaaggtggt aaaacactgg gtattaatga tactgaccac ttaatcactc ccggtggtta   55620
tcctcgtgtt agtttcgata ggaaaaataa catgatgggc tacagtagtg gtggttacaa   55680
attctttata ttaaacgtat cagacctatt ggctggtgtc aaaacggtta tgtatacgat   55740
tgatatgctt gattatgact tgttggtga tgatgatatt ttcaaggtc aagcattaga     55800 ttttccatac gttactgga gcgttggtaa tcaattctta ggtaaaacgt gttctttcta    55860
ttgcgtaaac attctacatc gtggcgaagt tatgcaccca tattatgacg cattaatcgg   55920
tttgggattg actggaaaaa taatcgaacc agaaagtctg tcattcgcaa caattaacgg   55980
taaaagaacc ctagttcatt catttaacgt taccccacca gatggaaatc cacccaagaa   56040
acaaatgcaa tatactaccg atattattta tcggccagca atgccagttg ttagcggtgg   56100
tggtgatgat ggtgatgata caggtaacga gtaggaggtt atcaaatggc aagaagtgca   56160
tttgtcgaag ttaatattac caatcctact aaactagcac aagattcaca agacactgcc   56220
gacaaagcag ttcaggggt tacagattta aatgacccta atttaatgtc tgtgattgaa    56280
aagcagaaca acgtcgtgca attgctggt ttaacatctc aatataacgt tcttgtgcag    56340
aacgccaaag atgaggggat tgacacaacc gctgtaacca cagcgtataa caacttaaac   56400
aaatttatgg ctgacgttct ggcagaccct gaccacgcta gtgacgtcga ccgtgtaaca   56460
tacaaaaaat atcaggacgc ttacaacgaa gaattgcaa agcttcaaaa cgcccttacaa   56520 aataacgcca acaacaaatt tgatagtgcc gccagtgcca cgagtcaagc ggcttcaaca   56580
```

| | |
|---|---|
| gctagtcaag cgtctagtca agcacagtct gctgttgatt acaccaacag tcagattgct | 56640 |
| tcacaagaaa gtgccgtttc agaagcttct aagaatgctt ccgaagcttc gtcaaaagcc | 56700 |
| aacagtgctc ttgacgcggc tagtggtgct aacgctgaaa tcactaagct aaaaggtggt | 56760 |
| tcaaccctaa ccatcgcaga gctagaagac ggtctaggta caaaagtttc taatgataca | 56820 |
| ttcacaacgt accaaacaca aactgctagt cagtttgcag aaacagttaa ggaagctgac | 56880 |
| tttacgacct atcaaactca aactagtaag ttaattgagt cgaaggttga taacggtacc | 56940 |
| tatcaaacag ataaaataca aacagctaaa gatatcgctt caaaagtttc ttctagcgat | 57000 |
| ttcgaaactt atcaaacaca aacagatggt atgattgcca gcaaggtttc taagaaggac | 57060 |
| gccaacaacg ttaacttaat accctactct agcaactttt cagattcatt agaaggttgg | 57120 |
| caattaatgg catggggtgc aactgataga aaactattag taaccactca caatttctat | 57180 |
| aaaaatggaa ctggaaagtt attatatctc aacacagcac agaatgcaac ttctgccgct | 57240 |
| ggttcattgc gtttctcggt attgccgaat actaaatata cgttccaatt taaggcgttt | 57300 |
| gcttcatcta acgttgttgg ggccaatgta tatttcttgt cacgtgctta tggttcgacc | 57360 |
| agtgattacg acacagctca tggcctattt aataatctgg taacttctcc atcgcacatt | 57420 |
| gaccagtaca cggttacatt tacaactggg gctaatgata atgagggtta catcagagtt | 57480 |
| gataatatag gttctaataa cggagcttct tctggtttgt tctttactga actcaaaatg | 57540 |
| gagccgggtg atactgcaac gaattatatt tacggtggtc aagattctat gatttctcaa | 57600 |
| atgtctaatg acattatttt aagagtaacc aaagacgact tgattgacca aatcaatatt | 57660 |
| caggccggta acaccttaat ttcatcgtagt ggtcagctaa cattatctgg taaaagtgtt | 57720 |
| tttcttgata gtgttgaccc cgttattatg aaaagtgcta atatcgacac gctccttgtt | 57780 |
| ggtaaaaaat taacagcggc agacattgcg gccaatactt ttacaactaa caatggaact | 57840 |
| ttcacggtag actcaaatgg tcttgtcaca gccacaagtt taattattcg tggttccaca | 57900 |
| aacctagttt ataacgcgtc attatctggt ggtaacggtt catatatccc ggggtggggt | 57960 |
| ataagtaata atggatatta ttcaaaccaa gtgttacacg atggcgtgcc atctattgga | 58020 |
| tatcataaca acacaggcgc tggggttttgg gcaaactttg cccaatctaa actatattca | 58080 |
| ttaaatggta aaactggtct tccttatagt gcgtcagttt ggttccttga ggttggtagt | 58140 |
| gatacaaacc tcaagtatca atttacactg gccttctttg atgccaacgg taaccgattg | 58200 |
| gatagtggat ttattggtaa cacgtggaac ggcattggct cacgacagga ttggcgttat | 58260 |
| gtgacaatca ataatgcaat ctcaccaagc aatgcagtat acgtcgctat ccaatattgg | 58320 |
| gcttataacg gtagtggata tggcttgttt agctcaccta tgctaactca gactgcacaa | 58380 |
| tcaactggtt accagccaga tacaggtaat gttgttagtg ctggtactgt tttaggtagt | 58440 |
| accattagcg gttcaaccat taatgcgact actttccacg gtggcgacct tatcaacaat | 58500 |
| gctaataaca ccagcaattt ctatccgttt actatcgagc ctactggtaa agcttctacg | 58560 |
| acgttgttta actcgatgga cgctctaagg acagagatga gtggtggcgg tttaagaacc | 58620 |
| atgtaccgtg ctataaatgc ttctggtagt caatacgagg cttatgatgg taattttagt | 58680 |
| ggtgatgcaa tctcgctaaa ctctggattt acgaatggta agatacgtc attctcgcaa | 58740 |
| tctgtttctg gtaatcaact aacaggtcaa gttgttctta gcccactaaa cggaatccac | 58800 |
| ctgtggggta gcacacaatc tattcatttt agcggtcttc aaatgaatgg tacaggtgtt | 58860 |
| acgtttaaca gttatggaaa tatcattgca gaccaagctt ctacttggtg gcgagttacc | 58920 |
| aatttttcag ggtctgatat tgcgaacttt ggtacagata cgtctggaaa caatcctatt | 58980 |

```
cagtttaatc gcgaactaga catcggaaat attcagatta atactggtca cacagttact    59040
agtgctgata agggcgctat tcactttgct aaaggtggag gtggaactgt tgatatttac    59100
gctggcgcag ttcattacac aagccttgtt aattcatcac tacttagtgt taagcgagac    59160
gtaaagaaag cagatactgc ttactgggca caattagtta atgcgattga tttagcaacc    59220
tatcaatata aaacagatga taacaccagt cacattaggc tatctggtat tgttgatgac    59280
attaacgaaa caaagcagtg gcagttacca gatatttta ttaatcgtga tgaaaatgga    59340
aaactaagcg gtgttgataa cagtgtgctg ttaaatgccg ctttagcaac tatccaagaa    59400
caacaaaaac aaatttctgc cttgaacggc cataatatgg aactagaatc aaggttaaac    59460
aaactggagg acaaattcaa tgaataacat cttaattacg aattataaac cagattacac    59520
aaataacatt atgactatta gtgttcagat taatacattg gcaattagtt cacaagtaag    59580
tattactatg gacgaattta acactgctat tgtaggtggt gtcgataatg ttaagttaaa    59640
agttcttaat acgctgattg acagtttaac agcattaaga ccaactagcg aagaaaaata    59700
ggaggaatta agctatgaaa tttgaattac aaaaccaatt cgttgcacca tcaattgaat    59760
ttctaaagag gttgccactt gctggctacc aatcaatcgc cagaacacgc ttaattaaaa    59820
tgttgtctaa taaaaatgat gagattgttg gtcttcaaaa agacctaatt aaagaatatg    59880
ccgataaaaa cgataaaggt gagttgattg ttaaagacgg tcaatacaac tttacacctg    59940
aaaatgatgt agctttcaga aaagcatatt ttaaattaat gatggagaat ggcgaaattg    60000
aaaaagctac ctattcacac cacaaagaag actgtcaaga cttcttatta aacgcagaca    60060
ttaatgtgtc tggcgatgaa gcaacgtgtt atgacgcatt atgtattgcg ttagatgttg    60120
attttgataa gcgatagaaa ggaatgattt agtttggcaa agacattaga atatgctgat    60180
acttctgctc aaactgttaa aattggcgat acaactacca gttttacaat ggtattgggt    60240
gaagacagca accctgttga cctcactaac gcaacaagta ttgttgccaa gctaggtaat    60300
agtaccggct acttaaagtc gcaaacagtt acttctgata atatcccaga cccgttatct    60360
ggtcaagtga ttattaaatt taattctgac tttatgagtg tcttccagc aggttcttac    60420 ttgctagaag tatgggtgac ttatgatagc ggagttgcta tctatcctag tggtgcttta    60480
acaggattta caattaataa taacattgaa agccaatctg gttcagttat cacatcaatt    60540
agttatgacg actttgtgga agcgatgaac aaagccgcca gcacgattgc taagggtgac    60600
aagggtgata ctgggcccat cgggccacaa ggcgtcatga ctaacgacca agtaaacaca    60660
gcaattgaca gtaaaataaa atacacctct attcctaacg gcactgattt atttactcac    60720
attaacaaca ctggtaacac agaacactta tgtaccaatt ctaatgcggc cgccatgtca    60780
ttattaaatt gtcctgtaac gacagtattc acgcttgata ttaaaactgc ttcaccagca    60840
aaccggccaa taggctctgc tggtggccct acgtgggttt ataatcaact tgaacttcac    60900
ccataccagt ctagcaacat ttacacaaca tctatcgaaa cagatggtaa cggtgcattt    60960
attactcacc catggaagaa gcttgttact caaacgtctg gtactttaga cgtaacgtca    61020
gcattttata agtctggcac aacaagtagt gtaagtgcat tgaactatgt gctaactggt    61080
aatgtattac atgtcagtgg ggtcgtctct ccaagtgctg atttagatgt tggtgccgct    61140
actacattgt tcaatttacc gtcttctatc ggtaatattt cagagactgt cgctgttact    61200
cagcagtctt ctggttggaa tttatactgt ttatcatggc aacctaacgg tgctgtttca    61260
gtattaaaac ataacattgc tggtaccgca acagctatta caactacaat gcagttgcaa    61320
```

-continued

```
gtgtgcgctg atattgttat taatcctaag taacaataaa atttgaattt tactctgaaa    61380
aaaatatcaa gaagtgaaca ttaacacaca aaaggagaca taaagatgaa taaacgacta    61440
aaacacgtac tatacggtac tgcattggca ttatcgttag gattatctgc ctctgttatt    61500
aatacgcaga atgccagtgc cgctaacacc agtgatggtg ctgttgttaa aaaagttgtc    61560
gatatttcag aatggcaagg taatgtttct tatcagaagg ctttagcttt aaaatctgaa    61620
acctcatttg taattgtccg tgttcaatac ggttctaatt acaaggatat tcagtataag    61680
aacacgattg ctaacctcga aaaagctggg acaccatatg gtgtttattc ttattcacgt    61740
tacgtgaacg cttctgacgc caagcaagaa gctaaagatt tgtacaatcg tgctaagaat    61800
gccaagttct tgttaacga cgcagaagaa gttactacga ctagtggctc ttattctagt    61860
gctgttaagg cttggggtac tgaaatgcaa agccttacca gcaagccagt tatcttatat    61920
tctggtagtt atttctacaa taactatatc ggaaccatga gcaactatga cgctttctgg    61980
gaagccaatt atagtaacca ttatctcaaa gacccagcat tatggcaata cacagattct    62040
ggttattcaa ctagtcttgg cttaggagtt gataccaaca aggttatcac gtctaagcac    62100
cctgtgaagt ggtggattgg ttctagtgcg gctgacaagc agaacgtaga caagtatcac    62160
gttggtggat tcaaggttgg cgacaagatt aaaattaatt ctaacgttgc taaatgggac    62220
gctggcgata ctaagactcc aattgatagt tctgtactaa agaagaccta tactgttggt    62280
caaatcaagc aagtaacgga aggtaaatct aaccaaatgc tcttgttaaa gagtggcaac    62340
actgttgttg gttggacgtt agccgaacac gttacgaagc aaggttctag ctcaaactct    62400
agctcatcta acagcaacaa ggcttccagc cagacctata accaaaacgg tacgttctat    62460
ccaaacacta ctctgaatgt tcgtactggc gctggtacca actattctaa ggtagccact    62520
tattacagtg gtgaaagtgt taagtataat caagtaatta ttaagtctga ttatgtatgg    62580
gctagatatt tacgttctaa cggttattat ggatatattg ctctaggtgt aaatggtggt    62640
gaaagctacg gtaagcgcgt tgttggttct tctcatacct attatacagt taaatctggt    62700
gacagtctat ggaagattgc caatgaccac gaaactacca ttagcaattt aactagcctt    62760
aatggtatct cgatgtatag cactatttat ccaaaccaac gactaattat tagctgataa    62820
gggaggttca ccacatggta ttaagtaaca ttattgccgc cgttccacct cattatttct    62880
ttggatataa tcttagtgaa tggacagaac tgattgccat tgtgagtgct tttttatcac    62940
tagtttcttg gttgttcaaa cgagttatta ttgacccgtt gatggaaaag attagtgact    63000
taggtgatag tattaagcag ttgtctgcta cgcagaatga agattctaac acatttatgc    63060
aaacgctaga gaagcacacc gaagaacttg agaagttaa aattacgatg gcaagacacg    63120
acgaagaatt aaggtctctc tggaagggga agaatagaac atgaacaaaa ttaaaactgc    63180
atttaacaac tttgtttctc aatttgtaaa aacatttgaa actaacaaga ctaaacctag    63240
ctactggtta caaattatcg gttctgtttt aatcatcgga ttagctgttg gttcagcatt    63300
ctttggtcta aagattgacc gtagtgatgt ccttatggta tttacggtta ttggttcagt    63360
gcttgcgttc gtaggtactg taacggataa ttctatcctt gaaaatgttg gtaacggtat    63420
taaaaacgat tctgatagtt taacgagtag tgaacaagac gttctcaaca aacttgtcga    63480
agctcaaaag gcgattgaaa atgcaaagac accaactgag caagcacaat tagcattaag    63540
tgccgctaat gaagctcaat ctgttgcaga tagcttagca aataaactat ctaaagaagc    63600
cgtttcagac gcagtcgtta gtacgcagga agtagcacag gccgtaacca gtgaatcaac    63660
aagtgtcgca gagccagcta gtgctgtatc agaagtacca gtaagcgaag ctcctagtga    63720
```

```
agctcctagt gaagctccta ctagcgaagc ttagtattaa tcctcacagt tatgtgaggg   63780
tacataaaaa tataaaaaag gaatggtgag atacaatgga actatttaat caagaagtct   63840
gggacacaaa agtcaaagat gaagataaag aagccttaga agattactta ttagagcttg   63900
aagccaacgg ccgggccgtt aagactcgtt atcagtataa ggcagatatt cgtggattct   63960
tatgctattc aaataagaaa tatccgaaca aaactgtaac acaattaaag cgtaaagact   64020
tccgtaattt cttttattta atgcaacgtg atggaaccag ccatgcacgt attaatcgtt   64080
ttcaaagtag tattagaaat tttctggaat atcttactat cagtgaagat tatgaatacg   64140
aaattaatca aatgcacgcc atcaagggggt taattaaaga acccgttaaa acacatactt   64200
acttaacaga tggtgaaata aatatgcttc ttgattattt aattcgtcat aagaagtatg   64260
aaaaggcatt gtttgttagt cttgcatatg aatcatgcgg tcgccgtaat gaaattattc   64320
aagttaaaaa gaatggattc gttaagtcaa atcaaacaaa taccgttatt ggtaagcgtg   64380
caaaacgatt tgagttgatt tattttaagc gcacacagca gattgcagac ctttatttaa   64440
atcaacgtgg cgacgatgat attgacagcc tatggatttc agactacggt gaagaacgtc   64500
acgtaattaa ctattctgtt ttttacgaat ggtgtaatca atttggacga atcttaacaa   64560
agcttactgg tcgcgaagtt actgttcacc ctcatgactt tagacggacg ggccttgaaa   64620
actattctgt tggtactcat catgtactag tagagtcaga taaaaaggca ttaccacttg   64680
aagtgctaaa actagttgct catcattcaa gttctgaaac cacagaaggc tacttaaaga   64740
accatgacga tgacaaattg agtaacgcat tcgggattga aattgaataa ggagtgtttt   64800
taattatgaa tacaattgaa gtaagagacg gagaagcaaa tctaacgcga gctgtcctat   64860
tcgattctcg tgcaaaggga atggcggcat tcttcacaaa gcgtgattta gatgattacc   64920
ttgaactatt atactacaaa aacaataaag atgacaccaa aatcaataag agaaaatata   64980
acacaatggt taaaaagtta aatattgacg agtatgacta ttgtggagta aagttaggat   65040
atttagtaaa ataagacacg aaaaggacac ccaactttgg gtgtcctttt tttatttgtc   65100
aaaacttaat ctaacttttc taccataccc attgattaac attactgttg tgctaaaatt   65160
ggcgtctcgt cgcaatctaa acgaatcctg ttggcgataa ccagtcaccg ctagtttgtt   65220 tcctcttttct aaccagctat cagatacaca gtgacgattt ttacctttac cagccatctc   65280
cttcttacca atttttgagt aaattgaacg ccctaatgat acgattgcta gaccatctgg   65340
tgtcaatagg ctaaccgttg atttcatatt attcttggct acaatagtac cggcaataat   65400
atgattctca tagattgaga atttacggcc atttctgcta gttacttctt tgattacttt   65460
aggttctggt tctaggtcat tgaatgattg atagtttagc attgcgctca atgatgacac   65520
ttcaagttcg tgttttttcgg ggtaaaagtt caatgcttca aaggcccagt gttctggatt   65580
tccttcacat tcttttagcc ataattcagc acaacgagta ttcctttcaa tttcaactgc   65640
ttctggagtt tttaaccatt cttttcaacg ttctgaaaat gagttaaacc acttattgta   65700
acgctttgtg tcgatattga tattgtctcc gtcgatactc cataagcttc cttctggttt   65760
cttctttaat ccttcctcat attgagtaat taaaggttcg atagtattaa tgaaccagcg   65820
cccaataggg ctatcaagct tgacagtatt atctttaacg tgtttcttca ttaggtaagc   65880
attcttttgt aactcatatt cttctgggat tttcttgtca attttgttaa tttgaaccgt   65940
agtcaatttc tgcttcggtt ctgtgatttt agagatatag tcaatcataa gttttctacg   66000
gtcattatca aagcaattca acgctccaga cttaattaaa agaatcatct tcttagtaga   66060
```

```
aaagacatct ttattcttat tcataaagtc atctaatgaa tcgtaaggac gattgttcat    66120
gatactttca atctcactaa ttccaatacc agaaatggca ttcagtccta gcaaaatatt    66180
ttttgattgt tttgtaatct taggaacaaa tccaatctca ctacgattaa tatctggata    66240
tgttactaac cctttcggta actgaccaat cgccgtcgct aatttattgt aatccgggtt    66300
tgacgtctca tctccatacg tctttgcatt gactgacaat acagcagttt gccagtagat    66360
agggtcaaat cgcttgcaga tattcatttc aaccattaac aatagtgtat atggtagtga    66420
atggctaacg ctgaatgcgt aacctgattg aatagcgatt tgtttatccc aaatatattt    66480
tgcaaactca tctctcaatc catacgtttt agccttttc aagaagaata cgtgttgttc    66540
ttcttgtttc ttcttgtctt tcttagcaat tgatttacgt aatttatttg cttcttctaa    66600
tgagtaccca gcaatcttta ataccatttg catgagtcgt tcttgtgagt tattaacacc    66660
cttgtaatca tcaagtaatt cgtgcattaa ttgttttca tcactagtga gaccagcatt    66720
atccatatct ttgtcccaat cattagggtt attctgataa cggatatatc tgtcaagtgc    66780
tagttcatcg tcgtcgccac cagtcaacct cataagacca ttggcagata ctaaggccaa    66840
gtagtcacga gcatttagtt tacgtagcgt tttgtaacca acagatgaac taaattcaaa    66900
ggcgtcaata acgtctccat tgaataacat cttgtacata tcaacgttag tcatatcaag    66960
tgcttctggg ccgaaatact tcatatacgt atcacgtaat gtatcttctt tattaatcct    67020
accatcttta atcagcatgt caatcgctga atgaatctta tctaacgctg acaatgatag    67080
aaagtcaaac ttaatcatac cagcatattc tgaatcatct gcatcaaatt gggtgacagc    67140
gatttgatga ggagtaacca tcattgcgtt gtgttcttca taaccattgt tggcaataag    67200
aactccagac gcgtgttcgc tacggccaac aactagccca aatagcccaa gaattgtttc    67260
tttcatcttt gggtacttat caacttcttc taataacttc ttagacggtt tacgaccatt    67320
tttctcatta ccaagtaacg cgtctgtaat gggccattca tcgtgaccat ctgctggtaa    67380
tagactaaca atatagttaa cttcattatt atcaatacct aaacctctac cagcatactt    67440
aatggctcca cgggttttaa tggtgctaaa tgtcgaaaaa ttaagaactt tattatcgcc    67500
ataaatttct ttgaccttat taataattcg ttcacgttta gttccctcgg tatcaacatc    67560
cacatctgga tagttagaag caatgttctc tgttacacgt tcggcagata agaagcgata    67620
atgtggtaag tcgtattta aagcgtcaac ttgcgttaag ccaatcaaat aattcaacag    67680
ccaacacgat gagctaccac ggccagggcc aactaaactt tgagtccaca taatatcaac    67740
aaaatcatgt tgagcaacaa ataagaact cattggttga ccaatattct cagtaatttt    67800
tacaagctcg ccaacttcta ggtcaagtcg ctttagataa tcattcttat ctttaagatt    67860
atgcttttca aggccatcta aggctagttt cattaaatag ctatcagttt tattactact    67920
ctcaaccatc tttttaatat taggtaaatc ttcgccatgg taaaagtcag cataagatgg    67980
attcgaaaac tctggaatgc gtccttgtgg tacgattggc tcatgctcta acgtatagtc    68040
ttgaacacgg tcaaaaatcg tgtgtagggt tgtaaatgct tttgtcagtg tatcgtcatc    68100
aaagaactca ataattctt ctacgctaaa caaatgagct gtatcataag ccattaaatc    68160
tctatcttga ttgcgagata gcaataaagc attgtgtact ggacgttgag cttcgtttaa    68220
atagtgagcg tctgtcgtaa taatatatgg aataccaatt gattcgctaa tctttttaag    68280
ccaattgttc acgataatct gttcttcatg gtggctaggc attagttcta aaaagacatt    68340
ccctttccca aaaacattga ccatccactt aatcatgcct tttactttt taaaatgtga    68400 attatcgtta tcttcgttgt atgacagaat ttcttgtgct acatacccgc caagacaggc    68460
```

```
cgtactagca atgacatgtc ctttatagtc gccactcttc attaatgatt cgatttcgtt    68520
gtagaagcta ggaacacgct ccgcaccatg atatacatga taatgtgacc atgctaatga    68580
tgattgcttc tgcaaaaact catgaccttt tttatcaaga gcattgataa gaaaatggtt    68640
gaacttaaaa ggctcgttgg attcctcggc cttttccatc tcactttggt caactaagta    68700
aatttcgttg cctaaaatga gcttaatatc tttaaactta tcttggtttg cgtggaagta    68760
tttctcagcc ttaatgtggt ctccaagcgc ttcgtgccca gtaaatgaaa ctgcttttaa    68820
gccaatttcg ttactataat caagcattte cttaacggtg attgaactat ccaaaaaacg    68880
cagattacta ctaaggtctg tgtgattatg aagactgcca tagccatatt taattaattc    68940
acttttatcc attttttattg tttctccttt ttactcatta gttgtttggc cttacaagca    69000
acttcacagc caaacttttc tctgatagcc tccactgtgc tctcatctgc gtatgtgaac    69060
catagaccgt gagtggtttt atatcggttt ttaagaacat tgctaatatt ccctacacta    69120
aatcctagaa cccgactggc tcatgttgt gattcaaacc atgacacttt ccaagttttt    69180
aaattcactg tgcatactgg ctcgccagat actcctacgg ctgttttccc gaatttctct    69240
ctatacgcaa cattatactc gtgtgagcac cattccaaat ttgaaacgtt attattctgc    69300
ggattattat ccctatggtt tatttctggc agatttccgg tatttggtaa gaagcactcc    69360
gccacgaggc ggtgggtgta tttgtgtaat tgtttttccgt ctacaacgaa ctgcacttgc    69420
atataccccc ctctcttgtc gttgcgttgt tgtttcagaa tcctacccttt tacgaacagt    69480 cttccatctc ctcgttttac atatctatca actgtcttta cctcgcctaa attactaacc    69540
ttaatagaat caaaatctgg gtgagtcttc caaacttcat tttcgctttt attcattatt    69600
attcctccct aatataatca tattaacaca attgaatgaa tatttcaatc taaataataa    69660
aaaagcggcc gcttgcagac ggccgaaaga ctagacatat aatttaactg attaactaaa    69720
ttttacttaa catatactaa acacataccg ttaagatatt taacataaat atctccattt    69780
ttatcaactt ccaagttttt gtaaatatta cccacatata taaaatcatc attaagatta    69840
tcaacaacca tagtgttaga agctgtttca tagtcatcac ttatgacttt ttcttctaat    69900
agtctatctt tagtattctt agacataagc aattgtgtat catcaaaata caaaatatta    69960
tcaacatcta taaagaaaaa gtcaattagt gtctcttgaa gtgccaaaga aattttatta    70020
ttcaactcca gattattttt taacattaca gtcctcctag cttctccatg tgttcatcta    70080
caatatgact aatttcgttg tcattgaatc ctgttgcttg taagattgca tacactgcca    70140
ataagtcttt ttcagcaaat gagcgtacag gagtttcact accagctacg ctataaccat    70200
atcctaaatc aactgcaatt gcagaaaatt ttggtgatga gtaaaacgtt gcaaagcttt    70260
caccatcaac agagccgtgg tttccgtgtg catgattcca cctacttcga ggatagtctc    70320
ctctaaaaac agaaaaataa cgtttatatt tactgttttt catcgctgtt tttctttggt    70380
gtgacgtctg tttcgaagta ttgttgcatt ttttcaattt tatcaactcc atctttaaaa    70440
atcttattat attcatcaat gtactctctg acgcttttta acttttttgtc attcttagca    70500 attgcatttt tagcataata tttttagggca tatgctaacc ctccgtgata tgttcggtcg    70560
atatgaatct ttgaactgct ctttgacttc gtgcggtgtt caagaataac cccagaagaa    70620
gaatgctcat tgtttacaat ccaccacgtc tggctcaatt taatttctaa actcattgta    70680
ttttcctttc ttatccagca atatctgata aaaagtcaga tagtgaatat cttttactta    70740
tatggtagtc tgttgccttt gcaatcgttg gagccgtagc tcttagaacc aaataaggaa    70800
```

```
ttacagatag aatgtataac gttccttta aaatgtacca tattgcgaca tcaattgcta   70860
aaagtgtcaa accaaacact ctaattatag cattaatcaa tttaagtcct ccttatattt   70920
gtaaagcaaa tgtgtcctga cagaattgaa ctgtcatcta cggtttagga gaccattatt   70980
ctatccaatt gaactaaaga cacatgttac tagactatgt ctagtataca gtatgttggc   71040
gctatgcgtg actctggagt cgaaccagtg cttcgggcc agttttactg tgcgcacccc   71100
gatagactac cgttatctta atcacgcgac tggttggtga ggatttgcac cccacatgat   71160
taacactttc caaatcgggc taaaaagtaa tcatgttaat ctgcctgcgt ctacctattc   71220
cgccacaacc aaggtaatta cctaatgcgt cctatgagat ttgaactcat aacttacgga   71280
ttagaagtcc gttgctctat ccagttgagc taagggcgct taacgtgaga gtaaccgtct   71340
ctcacaaaga tacaatttaa actctatcaa gtttaacctt acatattata tgttatcata   71400
atttttatta agtgtcaact attttttaaa atatcataaa ttaaattgtc gccaattgtc   71460
tcatcgccac gcatttctct aatatcgacc gtgctctttt taagcagacc agaatccaca   71520
aaattatcat atacaccctt gtttgtttca aacaagtcat ctcttaaatc tgacaaaact   71580
gcttctgttg ggttttcagc ttctgtcacg acatattgtt tgtgtaccac agaatcgtca   71640
acaccatcat attcattaac tagctcatat tcattcacta ataaatattt tttcatcttt   71700
acttatcctc ctcataggct aatttaaagt cataatttgt gattactcgt cgtggaagaa   71760
tcgaaagttc tttgtcctct acaatccagt cgccaatatt aatctttagg ttcccgttaa   71820
cggacgccag ataatattca tcgctttcac gaatattaag ttccgtatta taattaggtt   71880
tcttaaaaat ccaatactta tcgcacattt ctttactgcc gtcaaactgt tcagcaataa   71940
cggttccttt ttgtcggtat gttttcttca tattatattt cctctcaaac gtatatctaa   72000
ttaattatca taatattctt gttcgtaacg attgtcaacc ctaaatttgt taataaatcc   72060
agtcttaacc tttctgtaat taatttgctt cttggaatta aaggtgattt tacctttaga   72120
ccagcttgaa atataactaa tttcatagtg tgcaggaaca tgtcttgttt gaatcttcgt   72180 tccaaccttta aacaatttga tttttgagtt gaacttgctg tcaaaaatgt ctgggaataa   72240
attattcatt agagccttat ctgcgatatt tcggttatag atggcgacat cattaacatc   72300
tccatcttca caattagcca ttgtaccatt agatagactt atctctgtca gcttaatatt   72360
tcttttatac ctatattgat tagacgttac taagcttgta atataagcgt agctgtcgtg   72420
cgctggaaca tacttttgag acacaatggt gactacagag ttctcgtatg tttcattctt   72480
attatggata aagttaagta cgaatcctaa tagcactgtt aacaagacag aaataaccac   72540
aatcaacacc gactttgcgg taatattcct aatctttttc attttttcaaa ctcctctctt   72600 cctttaaacc atctatattc ataattgaca ctaagtcatc aacggttaaa cttctagcaa   72660
tatctctaat gttattaaga atttcttctt tacttttaa atactttgcc atctattaca   72720
cctcttcaaa catctcgatt aatctaccat aaaatactca ttttatttcc gttttttgac   72780
cgtgctaacg tcacaatacc ataatgacac ccacacgtta atcctaagca attctaaagc   72840
gtgtcaggta taattagtct aagattattt tagaacgtct ctagtaagct atcacgggat   72900 tatttttct tagtgactat tttaacgata aattttggt ggtttaggta aatttgtccg   72960
attgtacatt ttaattctgc accgattgcc acggatataa atatcatatc caagattact   73020 gaaatattt tcaatagccg tagctctttc gtcattcata cccgtcagaa aaaccacata   73080
agcgtaatca tcacccctta taatggcttt ttcgatttcc ctcttgatag tattggcctt   73140
tctgtctcgt tcaatattat ccagataata ctccatctgt ttttgcttgt tcttttgct   73200
```

```
gagcgacaat gcctgttcgg catttatgaa cttattcatt cttaccactc caatcaatct   73260
ttacgtgaat ttccgtaaaa tattgttgac tgtctagcga ttctgctggc agagggccga   73320
tttgtgtgtc tacctcaaaa tccaaaccat tgtttttcaa atttgaagaa taaaggtctt   73380
ggttcttaaa aatatcttct aacatctttt ctgaatcatc atataaacta gcatgattat   73440
taaataattt cccgtaaata tctaaagaat aatgcccgct aaatgcagaa tttttcataa   73500 cttttgactag catatcccag tattctggtt tcttctttct ttcaatcgcc ttttttagttg  73560 tttcttgaag ttccgtaaat aagtcttttt ccaattaaat catctcctta aaataataat   73620
accatgtttg aagatatatg tcaacaaaaa agagacgcac gttagtacgt ctctcaatct   73680
taatatgctg tttgtgacca cgcattcata ccttgagctt tgtataattg aatagcttca   73740
tctacctgtg acgatacgct accgtggcta gaacgcatta attgtaataa cccatacgca   73800
ccacttcctt ctgaattaga aatgtttacg ttacctttg attcacgatt gataatcgtg   73860
ctccatgttg atgaagattg accagtacga gaagccattt cttcggcaac ctgattaatt   73920
tctgattggc ttaattgacc agacgtcttt gacatcacag agctttgtga gctttgtgag   73980
ttttgttgtg gctgaacact tgtgtttgg ctttcagcac tcgaatagtt aactgcctta   74040
ttgccagtta ctgttggttg tgtttgtgcc ttcgccggtt gttcagtctt tactgtcggt   74100
actttgacag acactttagt tgtttgatta gcggtgttta cattgccatt aacttgtaac   74160
ttgtcgccga caaagattag gtttggatta cttaaagagt tctcatttac aatatcacta   74220
acagacgtcc catgctcgtg ggcgatttcg ctaacagtat ctccagcttg tacagtcacc   74280
atatctgcgc taactgtttg tactcctaat gccaaacctg ctactactgc cgcacttgct   74340
actaaagtat ttttattcat ttaaaataaa cctctttctt tatttgataa tatgattata   74400
ccatcttctt atttcatatt gattacaaca atattaatta ctctttacat aatatattgt   74460
ttgaaatttt gaccaactct tgcttattgg ctaattcaac gaataacgcc ttttcaaccct  74520 cctcaatttt cttttcttgg tctaaataat agtcttgacg tttcgtacta ttatgaactt   74580
cttgaagttc gtttagcgcc ttgataatgt tattgatttt tttattctgt ttacgaagca   74640
taccgtcaaa tgagctagtt aagctatcaa caacatcgtt aattacactt ctatttgctg   74700
actcattatt agaccgtttt gaaatccata caatatcatg taaagagtat gtagtaacca   74760
gactcttatt atgggtatct agtacaatcc taatttcttc atcatctaaa aacacgatgt   74820
tttcttgtgc ggtgcgacaa aaactaccac gagtaacaat attagtaatc catgctttca   74880
tgatagactt tgaaacacca aatctttgac gtgctcgttt cttaaaatgg tcacttctgg   74940
tataatcaat aacttcattt ctattaatca tagttcggtt tctccctcat cgaaattgca   75000
acttgaagct tcataaacac atctcttgct tcttcactat catactttcc aataaaagat   75060
acgttctcgg tatcttctga attatctata atgctaatca tcttttgtt attagaaaca   75120 ataaaaattg tttcatcgtt ttcattcaaa aaactattta catatttcat aatatagtcg   75180
aaggcgtctt gctcactact attctttcg aatttttat agtaaaagtt ctttgtctca    75240
ccattaacac aggcataagc aactctagca ccactgtaaa tcttattgta tgaaatataa   75300
attctcatag acataatgca acctccagac atttgttaac ctcacttaga acaccttctt   75360
ccagtcggtc aattctataa tataactggc taacgttaat cgtttgcacc tgttcacata   75420
gcgcagtgtt atgaatcatt tctccattgt ttggtaatcc aaagctaaca tgggttggta   75480
aattgtgttt attcttagta gttagtggga caattgtaat tgctggcgaa tatttattag   75540
```

```
ccatattatt tgacacaaca accactggac gttttccacg ctgaatggcg tcatgtgaac    75600
cttgccgtga ctccaaattt gcaaagaaaa tatctcctct tttaatcttt tctccattta    75660
ctagcatatg ccttatctcc ttttaataac ttgataatat gctatcatta tcatttcaac    75720
atgtcaacac cataatcaat ttttgtatt attataaaac ttcgatttta taccgtgtgt    75780
agtataaaat gttcaaacat agctaataat cctccggcta cgccccatcc caaaatcgct    75840
ccaaggctaa acaataacaa atacccagct aggaatagtg gttcgccgtc ttctgtttcc    75900
gatgtcataa ttccaatgga aataatgaca accaccacga atgcaacaaa cactcctagt    75960
atcactaaat accatgctgt ggtaaatggc tccatgattt cacttcctat ccaaatatta    76020
tcattataat ttatacgtgc caataccgta attactttt tgtattatta tagaagctaa    76080
tcatttcata tagtcctttt agctcggaaa catcattgcg attataaatt tcattcttaa    76140
tactgtcaat tttttcttta tagtatcgtc tttgctcaat ctgttttcc catctttctc    76200 caaaattctt atcatcagag atgtagtgta attcgataaa actaggacgc cacattttg    76260 gtaatattcc cgttgtcttt aaacgcatat ggctattcgt tcggtcatat ttgctatgtg    76320
aaaagtaaaa gcttgttttg ttcttttaa taacatatac ttttgacatt tttgcatgac    76380
cattatcatc aagatagaaa tcatataatt cttgaccaac ttctaggtct ctagcttttg    76440
ttaccactgt tgatttttca tttgttttg tcattattat ttactacctt tcttttttct    76500
ataataaaag cataccattt ctagtatgct ttgtcaaata tattttaatg tttaagctca    76560
acataaaggc tatcgtcgac aatttccgca taaagtccat gacaccttag tgcaaacaga    76620
atatcaactg gtttgtttgg taacggaaca gtaatcctat cgcttggata ttttgagtta    76680
actgccatat ccaatttatt gataatactt ttatattctt ctgtttcaga tatattttta    76740
acgagccgtt ctatattatc ggtatagatt tcatcataaa cttcgttttc tgacattcct    76800
tgtacgtctt taataagaac ctctctcagc gctggttcac caacaatatt tttagttcca    76860
cctgtttctt gatttattaa accactagca tatgataaat gaaaataaaa ctcatttaaa    76920
aataatccaa acaaaagcgc gaaaattata gaccataaga ggtattgctc ggttaagctc    76980
ttatcagaaa ttgaccacat taaggcatac accaatgcgc caattgatag cgccccaaaa    77040
agtacaaaaa agacaactga ccaataaaca ttttctttt tcgtcattat attattcctc    77100
atagttttcg ctaaattcca ttagtgcaaa aattgatggt aatgttccgt acttaataaa    77160
gtcattataa tcgtctgtca cagcactaac agatgaactc ccatctgtta atctcgcaat    77220
tgtcatgata atagttccgt catcgtattc taattcgtca tttgtaagag attccacgtc    77280
ttttctaaat tggttgacgt cttctttact atacacaact gaaatcaatc tattgtactt    77340
gtgcttactt agaacagcaa cgaaatcacc atcaccaata atgtcatcaa aattatctaa    77400
taaataatct ttaagtgtca ttagaatact ctcccctcaa acggcttatt cttaatatct    77460
aagaaattaa aactagctaa ctcactaata tcaataactt gtgcgcaccc cttagcaatc    77520
attagattaa gtggagcgcc actgtcaata acaacaataa ccggcttgtg ctgtgcgaaa    77580
gcatatccca tttcccacgc tgttccttcg tctacattgt tagtgtcaat taaagctaat    77640
acgacgtcag agtagtcaat tccaccgcaa tcaccaaaga atgttccaga ctgccactca    77700
acatcatata ataatgaatc gtcgtcttca acgaccagtc ctttatattg gttgtctagt    77760
ggaatatatg aattttaat atcaacggta tcgttatagg caagacttt ctttgctttc     77820 tctagcaggg acttttgtgc ttccgaaaac caaccagaag ctaaatatag tcgtttacta    77880
ctcattattt tgcctccgtt ttatcacgtt tcgttccata aagtatagcg agcttttaa    77940
```

```
tcgcttctgg gttaaatcca ctccacatac cagtttgcga ccaagaatac ccattgcttg   78000
attctaggta gttaaatgac acaataggtg cccgaccgaa tccttgttct ttaagattat   78060
caatctcttc ggcagacatt gaactaatgc tgttttcaaa atatgcaata tcgtaatgtt   78120
tgaatagctt cttagtcatg cggcactgcc cacaattttc ctttgtataa atgtcaactc   78180
tgatttgttc tttattttc gtcatattta tcgcctttct ttaattcata aatctcataa    78240
cgtaaatcat cattttctaa ttcaagttcg tctaggtgtt cttcaaggtc tgcaagttgg   78300
ctctgataat accaaatttg ttccattagt tccattctac tgctattgtc ttccatatta   78360
ttcaccataa tccaagccaa agattggttc cttgatagaa tacttagttg atagcatatc   78420
tgctatcagt ttaaattctc cagaagaaat accattacca atcatagaat gaatatcatt   78480
aataatttca ggaatattgt tattatcaat tttttccttt agctcactgt tttctttata   78540
caaggcgtca taatcttgtt caagtgaatc ataagagact tctagctctt ggacatcttg   78600
ctcactacaa tcaagttcat cgctaagtga ttcattctct gcttcaaggt catcaacctg   78660
ttgttctagt tctctaatat attcttcttc attatccatt acaatcactt ttcctttcaa   78720
aatataaaat cctagctatc aacgtattaa gtatacacga taactaggat aatgtcaata   78780
tattaattaa acttcttttg ctttattttt tgaaaaccac ttgctatcaa agaatgcaac   78840
taaatcattc ataatatata gcataggt gaagaaaaga acccaaacag catgtccttg      78900
catagcggtt actaaccata agacaattga actaagacct tgtgcaaacc agaaataata   78960
tgaagcccgg aatctgcgaa cagttaagat tgctccagtt aatccaatag ttgccgacaa   79020
agcgtcaata attggtcgag gactagttag gataaccgtg tcaagaccat acgtcacgat   79080
aaagaatcca atgaaagtta gcaaagtctg taaagcaaac ttagtgttca tcttccgtgg   79140
ttctaaatcc ttaccattgt tccaagtctt attaagcaat actggtaaat ctaacaggaa   79200
gatatagaat ccttgcataa tgatgtctga aaagttacta gtctttaatg ctacatagat   79260
taacatgata gcagaaacaa atccaagcac accattaatc ggacgaccat ttgtgatact   79320
caacgtacac gtaaatccaa tcaacccagc aacagtagaa gtcacgccaa tacctgtaat   79380
accatgtccc agaccgatat acagcaagaa tagccaacca attactaata agacataact   79440
agacttagtc cagccagtca tctgttcttt ataccatcgc caattgaaca cccgactaac   79500
tgactctgga ttgtagccta aatcattgac gctatttgta ttttgcaaaa ctaaaaacct   79560
cttcctattt ttattaggtc gtcaaaagac gccttatccc cgatttaacg gttttttataa 79620 cattactggt aatggtgtaa ttgttccatc gttgcttacg tctagcatta cctgtgagcg   79680
tgaagctcgg tagtgtagac gctctgaata gcttgtgggg ccgataagag agccagattg   79740
aataacaagt ccagattctt catgaactga taggctgtgg aaatggccgc caactaaagc   79800
gtcatatcta atattgtcga attgactaga aattgcaatt gtttctggtt tagaaatatt   79860
ttgtaagtct ccgtgaacaa acttaatgtt tgttccgtta acactgatat ggtcttccgt   79920
gaccttatca ggctctttta ccttaatatc gtaatcagtc tgttcaacaa tcatcttaat   79980
tgcttcattc aatactgttg agaacccatc gtctggcagg ttgtccttct tattaccatt   80040
tgctctatca tgatttccta gaatgccaga ataaattact ggaatgccag tgctacttgc   80100
gatgttaata atgaattcag aaatcagtct aattgctgtg ttaatttggt cagataactt   80160
taatgagatt tcatatgatt gattgtatct catataagca ccttcaatac tatcacctag   80220
gttctcaata taaattgctc ccggattgga gaaactagca tagtgaataa tcttatctgc   80280
```

```
atacttagcg agttctttttt tggcaattga ttcgtcatac tcatatccat cgacgtttac    80340
ttttgcccca atgtgaacgt cagataaaga tacaatcaga acattatcac cgccgtatga    80400
cttcggagta ccgctgtcta gttcattagg gataatagta ataccatctt ttaaagagcg    80460
ttttacatca cgcttaaaca gctccatatc cgcataatct cgacggctct tattaaattc    80520
acgacgcatt acttgtagtt ctcgcttttc aagcaacatt tcatcaatct ctttactaag    80580
cgcgtcacgt ttatggtcta attcattaga acgttgctgt tcaacagaat taattgtacc    80640
agttttgtat tgataccctt taatcaattg acggaatcct tcacattgtt ttgcgtcata    80700
cccatcttgc cgcaataaac gggctacttt gccccaattg gcacgcccgt tatctcgctg    80760
taattcagtt ttatattcag cggccttttc cagaccgaca tcatcaattt cgtgtgtttt    80820
acctttatta tcagtataag ttgccattaa actctccctc tagtaacctt tcttttttgc    80880
cgtttcagtt agttctgaca agataattgc caaatcttct gaacggttgt cagaaagttc    80940
attaaccttg tggcctttgc ctaaggtctt ttcaacgatt gttgtcagcg tcttaatatc    81000
attgttcttt tggaacaaga ttgcaaccgc ctttgtcttt tctaataggt ctgagaagtc    81060
atattgaacg tccttggcgt cagcgtgtag cactttcttt tcggtagttt cgtcataatt    81120
gctaccaaga actcgtgaaa cttccttctt atatgcttct gcactaaatg gaatgattgg    81180
tttaacaccc ttaaacgtcg taccagcttc gtattgaagc gttccgcgta agtgtaatac    81240
gcgttgttct tctccattta ctaagttatt ttcagcatat agaatattat caaccatttt    81300
agtgactggt gacaagcctt tttccttcaa atctggagaa attttagtaa attcaaccat    81360 ctgtttttcca tcattagcct tagatagaac agcgtcagga atggcattca tttcattaga    81420
atcaatatat ggaatcttga caatcttttc agtagaatgt gatacaaaga tatttgtata    81480
tggtaatgat tctaattctt tcaaacctcg gaaccacact tcactaagac gagtatggtc    81540
tcgaccataa cctacgtcgc catcaccaac actaaattcg tcaaattggg aagctgtaaa    81600
cttgcttgca tagcgataaa ggttttcaac agtatcaatt gaaactgcgt cgtacatttc    81660
ttgaacttct ttacgtttca attgagatag aacttgctta aattcacccc aagtagaaat    81720
gtattgaacc atcgcaccat ctaacgcccc atatcgacgc tccgtcataa tattcagaac    81780
tctcggaaac aattcgttaa cgaacgttgt tttaccaatc ttagatggcc catataacaa    81840
caggctatag ctcgaaggct cagtagaaac tttgttagca gtaatcttag tcaaatcaat    81900 cattttata ctttcactcc tattatgata aatctagtta aacaaattaa tcttctttaa    81960
atcatcaaaa tttagttcaa cgtcaaatgt attagctaat tgttcagatg ttagtagcat    82020
aattt                                                                82025
```

LACTOBACILLUS PLANTARUM BACTERIOPHAGE LAC-PLP-1 AND USE THEREOF FOR INHIBITING LACTOBACILLUS PLANTARUM PROLIFERATION

CROSS-REFERENCE TO RELATED APPLICATIONS

This application is a U.S. National Phase Application of International Application No. PCT/KR2016/000030, filed Jan. 5, 2016, which claims priority to Korean Application No. 10-2015-0014188, filed Jan. 29, 2015, each of which are hereby incorporated by reference in their entirety.

REFERENCE TO SEQUENCE LISTING

The Sequence Listing submitted Jul. 14, 2017, as a text file named "08162_0036U1_Sequence_Listing.txt," created on Jun. 21, 2017, and having a size of 104,444 bytes is hereby incorporated by reference pursuant to 37 C.F.R. § 1.52(e)(5).

BACKGROUND OF THE INVENTION

1. Field of the Invention

The present invention relates to a bacteriophage isolated from the nature that infects and kills *Lactobacillus plantarum* cells, and a method for preventing and treating the contaminations of *Lactobacillus plantarum* in a process for producing bio-ethanol by using a composition comprising the bacteriophage as an active ingredient. More particularly, the present invention relates to a Siphoviridae bacteriophage Lac-PLP-1 that is isolated from the nature and can kill *Lactobacillus plantarum* cells specifically, which has a genome represented by the nucleotide sequence of SEQ. ID. NO: 1 (Accession NO: KCTC 12665BP), and a method for preventing and treating the contaminations of *Lactobacillus plantarum* in a process for producing bio-ethanol by using the composition comprising the bacteriophage as an active ingredient.

2. Description of the Related Art

*Lactobacillus plantarum* is a nonmotile Gram-positive bacillus and has 0.9~1.2 μm×3~8 μm of size. *Lactobacillus plantarum* is a kind of Lactic Acid Bacteria (LAB) which ferments arabinose, sucrose, glucose, fructose, galactose, maltose, dextran and the like, to generate lactic acids. In general, *Lactobacillus plantarum* distributes widely in nature and is often isolated from dairy products (milk, cheese, butter), kefir, fermented crops, kimchi and the like. *Lactobacillus plantarum* has a feature to resist gastric acids and bile acids more strongly than other bacteria in a human body. Besides, it is reported as a beneficial bacterium to increase the secretion of cytokines in human immunocytes and decrease inflammation inducing factors, thereby helping to alleviate irritable bowel syndrome and improve atopic and allergic dermatitis. *Lactobacillus plantarum* genome is also elucidated to generate an antibiotic substance referred to as lactolin that is effective to suppress herpes virus.

Unfortunately, *Lactobacillus plantarum* is also reported as a dominant bacterium contaminated in a process for producing bio-ethanol in spite of such beneficial functions. When this contamination occurs during producing bio-ethanol, *Lactobacillus plantarum* could consume indispensable sugars, and thereby reduce the final productivity of bio-ethanol a lot. Moreover, it may generate organic acids in a large scale to inhibit the growth of yeast, a bio-ethanol-producing strain, which plays adverse actions in the process for producing bio-ethanol. Therefore, it is urgently requested to develop an effective method for treating the contaminations of *Lactobacillus plantarum* in this process.

Nowadays, the advent of the era of high oil prices is expected, due to increased consumption of petroleum and depletion of fossil fuels. Accordingly, it becomes more important to find alternative energy sources world-widely. Bio-ethanol is a potential bio-fuel to reduce the dependence upon petroleum. Bio-ethanol is produced by fermenting starch crops including sugarcane, wheat, corn, potato, barley and the like. In contrast to fossil fuels, bio-ethanol is advantageous not to generate any environment-pollution substances after being used. Besides, it is further advantageous to be applied for transport fuels, compared to other alternative sources. Considering such merits of bio-ethanol, it is required to solve this problem, the contaminations of *Lactobacillus plantarum* in the process for producing bio-ethanol, which could have an industrial significance since influencing directly on the improvement of its productive yield.

Recently, the use of bacteriophages has drawn our attention as a new way of treating bacterial contaminations. Particularly, the reason of our high interest in bacteriophages is because bacteriophage-based treatment is a nature-friendly method.

Bacteriophages are an extremely small microorganism that infects bacteria, which are called phage in short. Once bacteriophage infects bacteria, the bacteriophage is proliferated in the inside of the bacterial cell. After full proliferation, the progenies destroy the bacterial cell wall to escape from the host, suggesting that the bacteriophage has bacteria killing ability. The bacteriophage infection is characterized by high specificity, so that a certain bacteriophage infects only a specific bacterium. That is, the bacterium that can be infected by certain bacteriophage is limited, suggesting that bacteriophage can kill only a specific bacterium and cannot harm other bacteria.

Bacteriophage was first found out by an English bacteriologist Twort in 1915 when he noticed that *Micrococcus* colonies melted and became transparent by something unknown. In 1917, a French bacteriologist d'Herelle found out that *Shigella dysenteriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella Typhi*, and *Vibrio cholerae* have been continuously identified. Owing to the unique capability of bacteriophage to kill bacteria, bacteriophages have been studied and anticipated as a method to treat bacteria. However, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new anti-bacterial agent that can replace the conventional antibiotics.

Furthermore, the recent regulation of using antibiotics is fortified by the government world-widely. The interest on bacteriophages is increasing more and also industrial applications are increasily achieved.

Therefore, the present inventors tried to develop a composition applicable for the prevention or treatment of *Lactobacillus plantarum* contaminations by using a bacteriophage that is isolated from the nature and can kill *Lactobacillus plantarum* cells selectively, and further to establish a method for preventing or treating the contaminations of *Lactobacillus plantarum* in a process for producing bio-ethanol by using the composition. As a result, the present inventors isolated bacteriophages suitable for this purpose and secured the nucleotide sequence of the genome that distinguishes the bacteriophage of the present invention from other bacteriophages. Then, we have developed a composition comprising the isolated bacteriophage as an active ingredient, and confirmed that this composition could be efficiently used for the prevention and treatment of *Lactobacillus plantarum* contaminations in a process for producing bio-ethanol, leading to the completion of the present invention.

SUMMARY OF THE INVENTION

It is an object of the present invention to provide a Siphoviridae bacteriophage Lac-PLP-1 that is isolated from the nature and can kill specifically *Lactobacillus plantarum*, a dominant bacterium contaminated in a process for producing bio-ethanol, which has the genome represented by the nucleotide sequence of SEQ. ID. NO: 1 (Accession NO: KCTC 12665BP).

It is another object of the present invention to provide a composition applicable for the prevention of *Lactobacillus plantarum* contaminations, which comprises the isolated bacteriophage Lac-PLP-1 capable of infecting and killing *Lactobacillus plantarum*, a dominant bacterium contaminated in a process for producing bio-ethanol, as an active ingredient.

It is another object of the present invention to provide a composition applicable for the treatment of *Lactobacillus plantarum* contaminations, which comprises the isolated bacteriophage Lac-PLP-1 capable of infecting and killing *Lactobacillus plantarum*, a dominant bacterium contaminated in a process for producing bio-ethanol, as an active ingredient.

It is another object of the present invention to provide a method for preventing the contaminations of *Lactobacillus plantarum* by using the composition which comprises the isolated bacteriophage Lac-PLP-1 capable of infecting and killing *Lactobacillus plantarum*, a dominant bacterium contaminated in a process for producing bio-ethanol, as an active ingredient, and is applicable for this prevention in a process for producing bio-ethanol.

It is the other object of the present invention to provide a method for treating the contaminations of *Lactobacillus plantarum* by using the composition which comprises the isolated bacteriophage Lac-PLP-1 capable of infecting and killing *Lactobacillus plantarum*, a dominant bacterium contaminated in a process for producing bio-ethanol, as an active ingredient, and is applicable for this treatment in a process for producing bio-ethanol.

To achieve the above objects, the present invention provides a Siphoviridae bacteriophage Lac-PLP-1 that is isolated from the nature and can kill *Lactobacillus plantarum* cells specifically, which has the genome represented by the nucleotide sequence of SEQ. ID. NO: 1 (Accession NO: KCTC 12665BP), and a method for preventing and treating the contaminations of *Lactobacillus plantarum* using a composition comprising the bacteriophage as an active ingredient.

The bacteriophage Lac-PLP-1 has been isolated by the present inventors and then deposited at Korean Collection for Type Cultures, Korea Research Institute of Bioscience and Biotechnology in Aug. 21, 2014 (Accession NO: KCTC 12665BP).

The present invention also provides a composition applicable for the prevention or the treatment of *Lactobacillus plantarum* contaminations, which comprises the bacteriophage Lac-PLP-1 used to prevent and treat the contaminations of *Lactobacillus plantarum* in a process for producing bio-ethanol, as an active ingredient.

Since the bacteriophage Lac-PLP-1 included in the composition of the present invention kills *Lactobacillus plantarum* cells efficiently, it is regarded as effective to prevent or treat the contaminations of *Lactobacillus plantarum*. Therefore, the composition of the present invention can be utilized in order to prevent and treat the contaminations of *Lactobacillus plantarum* in a process for producing bio-ethanol.

In this specification, the term "treatment" or "treat" indicates (i) to inhibit the growth of *Lactobacillus plantarum* contaminated in a process for producing bio-ethanol effectively; and (ii) to reduce *Lactobacillus plantarum* contaminated in a process for producing bio-ethanol.

In this description, the term "isolation" or "isolated" indicates all the actions to separate the bacteriophage by using diverse experimental techniques and to secure the characteristics that can distinguish this bacteriophage from others, and further includes the action of proliferating the bacteriophage via bioengineering techniques so as to make it useful.

In one embodiment, the composition of the present invention can be realized in a stable form comprising the bacteriophage without any limitation. For example, it can be prepared in a liquid or solid form and the solid form can be prepared in various forms such as powder, pellet or the like. But it should not be limited to.

The composition of the present invention can further comprise various ingredients in order to improve the stability or the activity of the bacteriophage. Particularly, the composition of the present invention can comprise various salts, pH buffering agents, stabilizers, detergents, wetting agents, emulsifiers, suspending agents, preservatives etc., but not limited to.

In the composition of the present invention, the bacteriophage Lac-PLP-1 is included as an active ingredient. At this time, the bacteriophage Lac-PLP-1 is included at the concentration of $1\times10^1$ pfu/ml~$1\times10^{30}$ pfu/ml or $1\times10^1$ pfu/g~$1\times10^{30}$ pfu/g, and preferably at the concentration of $1\times10^4$ pfu/ml~$1\times10^{15}$ pfu/ml or $1\times10^4$ pfu/g~$1\times10^{15}$ pfu/g.

The composition of the present invention can be formulated by the method that could be performed easily by those in the art by using a carrier and/or excipient acceptable in the art, in the form of unit dose or in a multi-dose container.

The composition of the present invention can be added and used in a process for producing bio-ethanol according to application modes, but not limited to. It can be used in any procedure adopted from pre-treatment of raw material, liquefaction, glycosylation and fermentation, and preferably fermentation, in the process for producing bio-ethanol.

The composition of the present invention or the method for prevent and treat the contaminations of *Lactobacillus plantarum* can be applied for any process for producing bio-ethanol regardless of using sugarcane, corn, girasol, plants and the like as raw material.

Advantageous Effect

The composition comprising the bacteriophage Lac-PLP-1 of the present invention as an active ingredient can be used to prevent and treat the contaminations of *Lactobacillus plantarum* in a process for producing bio-ethanol, which prevents loss of sugars caused by the contaminations and thereby increases the productive yield of bio-ethanol.

In addition, the method for prevent and treat the contaminations of *Lactobacillus plantarum* in a process for producing bio-ethanol by using the composition comprising the bacteriophage Lac-PLP-1 of the present invention as an active ingredient, is advantageous to be nature-friendly, compared with the conventional methods based on chemical material including conventional antibiotics etc. When exploiting the conventional methods, the chemical material such as conventional antibiotics could remain within byproducts through the procedure, so that the application of products for feeds of livestock, fertilizers or the like could be restricted. However, the method of the present invention using the composition comprising the bacteriophage Lac-PLP-1 as an active ingredient, facilitates the application of products for feeds of livestock, fertilizers or the like without any limitation. In the meantime, the occurrence of antibiotics-resistant bacteria is increasing recently so as to reduce the effectiveness of antibiotics continuously in those conventional methods. The composition of the present invention and the method of the present invention are expected to settle such a problem of antibiotic resistance simply, because the bacteriophage Lac-PLP-1 included as an active ingredient in the composition of the present invention gives the antibiotic efficacy against *Lactobacillus plantarum* regardless of the presence of antibiotic resistances.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
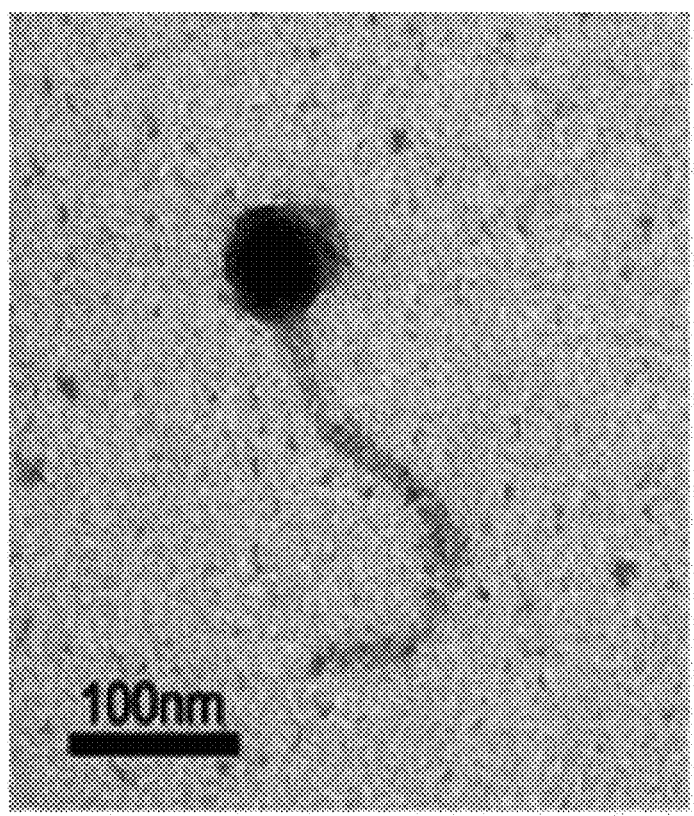
FIG. 1 is an electron micrograph showing the morphology of the bacteriophage Lac-PLP-1.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing *Lactobacillus plantarum*

Samples were collected from the nature to screen the bacteriophage capable of killing *Lactobacillus plantarum*. The *Lactobacillus plantarum* used for the bacteriophage isolation herein were the one that had been isolated by the present inventors and identified as *Lactobacillus plantarum* previously.

The isolation procedure of the bacteriophage is described in detail hereinafter. The collected sample was added to the MRS (deMan Rogosa and Sharpe Broth) medium (proteose peptone NO: 3, 10 g/L; beef extract, g/L; yeast extract, 5 g/L; dextrose, 20 g/L; polysorbate 80, 1 g/L; ammonium acetate, 2 g/L; sodium acetate, 5 g/L; magnesium sulfate, 0.1 g/L; manganese sulfate, 0.05 g/L; dipotassium phosphate, 2 g/L) inoculated with *Lactobacillus plantarum* at the ratio of 1/100, followed by standing culture at 30° C. for 3~4 hours. Upon completion of the culture, centrifugation was performed at 8,000 rpm for 20 minutes and supernatant was recovered. The recovered supernatant was inoculated with *Lactobacillus plantarum* at the ratio of 1/100, followed by standing culture at 30° C. for 3~4 hours. When the sample contained the bacteriophage, the above procedure was repeated total 5 times in order to increase the titer of the bacteriophage. After repeating the procedure 5 times, the culture solution proceeded to centrifugation at 8,000 rpm for 20 minutes and the resulting supernatant was recovered. The recovered supernatant was filtrated by using a 0.45 μm filter. The obtained filtrate was used in spot assay for examining whether or not the bacteriophage capable of killing *Lactobacillus plantarum* was included therein.

Spot assay was performed as follows; MRS medium was inoculated with *Lactobacillus plantarum* at the ratio of 1/100, followed by standing culture at 30° C. for overnight. 3 ml (2.0 of $OD_{600}$) of the culture broth of *Lactobacillus plantarum* prepared above was spread on the MRS-A (deMan Rogosa and Sharpe Agar) medium (proteose peptone NO: 3, 10 g/L; beef extract, g/L; yeast extract, 5 g/L; dextrose, 20 g/L; polysorbate 80, 1 g/L; ammonium acetate, 2 g/L; sodium acetate, 5 g/L; magnesium sulfate, 0.1 g/L; manganese sulfate, 0.05 g/L; dipotasium phosphate, 2 g/L; agar, 15 g/L) plate. The plate stood in a chamber for about minutes to dry. After drying, 10 μl of the resulting filtrate was spotted directly onto the surface of the *Lactobacillus plantarum* lawns and dried for about 30 minutes. Following drying, the plate was incubated at 30° C. for a day and then, examined for the formation of clear zones on the surface of the bacterial lawns. If a clear zone was generated where the filtrate was dropped, it could be judged that the bacteriophage capable of killing *Lactobacillus plantarum* was included in the filtrate. Through the above procedure, the filtrate containing the bacteriophage having the killing ability of *Lactobacillus plantarum* could be obtained.

After that, the bacteriophage was isolated from the filtrate confirmed above to have the bacteriophage capable of killing *Lactobacillus plantarum*. The conventional plaque assay was used for the isolation of pure bacteriophages. In detail, a plaque formed in the course of the plaque assay was picked up by using a sterilized tip, which was then added to the culture solution of *Lactobacillus plantarum*, followed by standing culture at 30° C. for 4~5 hours. Upon completion of the culture, centrifugation was performed at 8,000 rpm for 20 minutes to obtain supernatant. The recovered supernatant was inoculated with *Lactobacillus plantarum* culture at the ratio of 1/50, followed by standing culture again at 30° C. for 4~5 hours. To increase the titer of the bacteriophage, the above procedure was repeated at least 5 times. Then, centrifugation was performed at 8,000 rpm for 20 minutes to obtain supernatant. Plaque assay was performed with the obtained supernatant. In general, the pure bacteriophage isolation is not completed by one-time procedure, so the above procedure was repeated by using the plaque formed above. After at least 5 times of repeated procedure, the solution containing the pure bacteriophage was obtained. The procedure for the isolation of the pure bacteriophage was generally repeated until the generated plaques became similar in sizes and morphologies. And the final pure bacteriophage isolation was confirmed by the observation under electron microscope. Until the pure bacteriophage isolation was confirmed under electron microscope, the above procedure was repeated. The observation under electron microscope was performed by the conventional method. Briefly, the solution containing the pure bacteriophage was loaded on copper grid, followed by negative staining with 2% uranyl acetate. After drying thereof, the morphology was observed under transmission electron microscope. The electron micrograph of the bacteriophage isolated in the present invention is presented in FIG. 1. From the morphological observation, the bacteriophage isolated above was identified as belonging to the family Siphoviridae.

The solution containing the pure bacteriophage confirmed above proceeded to purification. The culture broth of *Lactobacillus plantarum* was added to the solution containing the pure bacteriophage at the volume of 1/50 of the total volume of the bacteriophage solution, followed by culturing again for 4~5 hours. Upon completion of the culture, centrifugation was performed at 8,000 rpm for 20 minutes to obtain supernatant. This procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 ml of the filtrate until reaching 10% PEG 8000/0.5 M NaCl, which stood at 4° C. for 2~3 hours. Then, centrifugation was performed at 8,000 rpm for 30 minutes to obtain the bacteriophage precipitate. The resulting bacteriophage precipitate was resuspended in 5 ml of buffer (10 mM Tris-HCl, 10 mM $MgSO_4$, 0.1% Gelatin, pH 8.0). This solution was called as the bacteriophage suspension or bacteriophage solution.

As a result, the pure bacteriophage purified above was collected, which was named as the bacteriophage Lac-PLP-1 and then deposited at Korean Collection for Type Cultures, Korea Research Institute of Bioscience and Biotechnology in Aug. 21, 2014 (Accession NO: KCTC 12665BP).

Example 2: Separation and Sequence Analysis of the Bacteriophage Lac-PLP-1 Genome The genome of the bacteriophage Lac-PLP-1 was separated as follows. The genome was separated from the bacteriophage suspension obtained in Example 1. First, in order to eliminate DNA and RNA of *Lactobacillus plantarum* included in the suspension, DNase I and RNase A were added 200 U each to 10 ml of the bacteriophage suspension, which was incubated at 37° C. for 30 minutes. 30 minutes later, to remove the DNase I and RNase A activity, 500 μl of 0.5 M ethylenediaminetetraacetic acid (EDTA) was added thereto, which was incubated for 10 minutes. The suspension was further incubated at 65° C. for 10 minutes and then added with 100 μl of proteinase K (20 mg/ml) to break the outer wall of the bacteriophage, followed by incubation at 37° C. for 20 minutes. After that, 500 μl of 10% sodium dodecyl sulfate (SDS) solution was added thereto, followed by incubation at 65° C. for 1 hour. 10 ml of the mixture of phenol:chloroform:isoamylalcohol in a ratio of 25:24:1 was added thereto, followed by mixing well. The mixture was centrifuged at 13,000 rpm for 15 minutes to separate each layer. The upper layer was obtained, to which isopropyl alcohol was added at the volume of 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the bacteriophage Lac-PLP-1 genome.

The nucleotide sequence of the genome of the bacteriophage Lac-PLP-1 obtained above was analyzed by Next Generation Sequencing (NGS) using illumina Mi-Seq device at National Instrumentation Center for Environmental Management, Seoul National University. As a result, it is suggested that the final genome of bacteriophage Lac-PLP-1 have 82,025 bp of size and the nucleotide sequence of the whole genome has SEQ. ID. NO: 1.

Similarity of the genomic sequence of the bacteriophage Lac-PLP-1 obtained above with the previously reported bacteriophage genome sequences was investigated by using BLAST. From the BLAST result, it is noted that the genomic sequence of bacteriophage Lac-PLP-1 had 89% homology with the of *Lactobacillus* bacteriophage ATCC 8014-B2 (GenBank Accession NO: JX486088.1) and 82% homology with that of *Lactobacillus* bacteriophage LP65 (GenBank Accession NO: AY682195.1), but genomic sequences having more than 90% homology were not found.

Based upon this result, it is concluded that the bacteriophage Lac-PLP-1 should be a novel bacteriophage not reported previously.

Example 3: Investigation of Killing Ability of the Bacteriophage Lac-PLP-1 Against *Lactobacillus plantarum*

Figure 2:
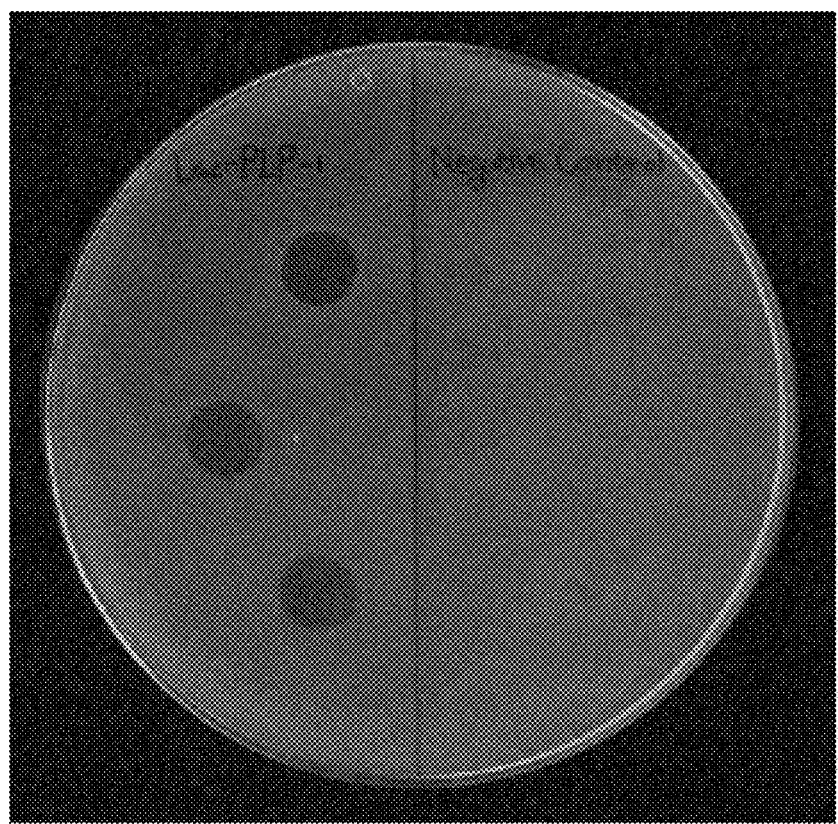
FIG. 2 is a photograph illustrating the capability of the bacteriophage Lac-PLP-1 to kill *Lactobacillus plantarum*. The clear zone on the dish is the formation of plaque by lysis of bacteria cells.

The killing ability of the isolated bacteriophage Lac-PLP-1 against *Lactobacillus plantarum* was investigated. To do so, the formation of clear zone was observed by the spot assay by the same manner as described in Example 1. The *Lactobacillus plantarum* used for this investigation were total 12 strains which had been isolated and identified as *Lactobacillus plantarum* previously by the present inventors. The bacteriophage Lac-PLP-1 demonstrated the killing ability against 10 strains of the *Lactobacillus plantarum* used in this experiment. The representative result of the killing ability test is shown in FIG. 2. In the meantime, the activity of the bacteriophage Lac-PLP-1 to kill *Staphylococcus aureus, Enterococcus faecalis, Enterococcus faecium, Streptococcus agalactiae, Streptococcus uberis, Haemophilus parasuis, Bordetella bronchiseptica,* and *Escherichia coli* was also investigated. As a result, it is decided that the bacteriophage Lac-PLP-1 did not have the killing activity against these microorganisms.

Therefore, it is confirmed that the bacteriophage Lac-PLP-1 had the specific killing ability against *Lactobacillus plantarum* and a broad antibacterial spectrum against *Lactobacillus plantarum*, suggesting that the bacteriophage Lac-PLP-1 of the present invention could be used as an active ingredient for the composition for preventing and treating the contaminations of *Lactobacillus plantarum*.

Example 4: Preventive Effect of Bacteriophage Lac-PLP-1 on the Contaminations of *Lactobacillus plantarum*

The bacteriophage Lac-PLP-1 was investigated under a similar bio-ethanol-producing condition whether it could be used to prevent the contaminations of *Lactobacillus plantarum* or not. 100 mL of molasses medium (16% total sugars, 0.046% $KH_2PO_4$, 0.225% urea) was added to 4 of 300 mL erlenmeyer flasks respectively. Then, the bacteriophage Lac-PLP-1 suspension prepared by the same manner as described in Example 1 was added to only 2 flasks to adjust the concentration of bacteriophage at $1\times10^6$ pfu/mL, while the other 2 flasks remained intact. After that, *Lactobacillus plantarum* cells were added to all flasks to reach $1 \times 10^4$ cfu/mL. The resulting solutions were cultivated at 30° C. for 16 hours. Then, 100 μL of the solution was collected from each flask, ten-fold serially diluted in physiological saline solution, spread onto MRS-A medium plates respectively and then cultivated at 30° C. in a plate incubator for overnight. Upon completion of overnight culture, the number of colonies formed was counted. Then, based upon the count of colonies, the concentration of *Lactobacillus plantarum* was calculated in each flask. The results are as follows.

TABLE 1

Suppresion of *Lactobacillus plantarum* contamination

| Item | Concentration of *Lactobacillus plantarum* cells |
|---|---|
| Flask 1 (−bacteriophage solution) | approximately $10^7$ cfu/mL |
| Flask 2 (−bacteriophage solution) | approximately $10^7$ cfu/mL |
| Flask 1 (+bacteriophage solution) | approximately $10^2$ cfu/mL |
| Flask 2 (+bacteriophage solution) | approximately $10^2$ cfu/mL |

The above results indicate that the bacteriophage Lac-PLP-1 not only inhibited the growth of *Lactobacillus plantarum* but also could kill them. Therefore, it is concluded that the bacteriophage Lac-PLP-1 could be used as an active ingredient of the composition in order to prevent the contaminations of *Lactobacillus plantarum*.

Example 5: Effect of the Treatment with Bacteriophage Lac-PLP-1 on the Contaminations of *Lactobacillus plantarum*

The bacteriophage Lac-PLP-1 was investigated under a similar bio-ethanol-producing condition whether it could be used to treat the contaminations of *Lactobacillus plantarum* or not. 100 mL of molasses medium was added to 4 of 300 mL erlenmeyer flasks respectively and inoculated with yeast cells to reach $5 \times 10^7$ cfu/mL. Then, *Lactobacillus plantarum* (lx $10^4$ cfu/mL) was inoculated to all erlenmeyer flasks. After inoculation, the bacteriophage Lac-PLP-1 suspension prepared by the same manner as described in Example 1 was added to only 2 flasks to adjust the concentration of bacteriophage at $1 \times 10^7$ pfu/mL, while the other 2 flasks remained intact. The resulting solutions were cultivated at 30° C. for 24 hours. Then, 100 μL of the solution was collected from each flask, ten-fold serially diluted in physiological saline solution and spread onto MRS-A medium plates respectively. The resulting plates were cultivated at 30° C. in a plate incubator for 24 hours. Upon completion of overnight culture, the number of colonies formed was counted. Then, based upon the count of colonies, the concentration of *Lactobacillus plantarum* was calculated in each flask. The results are as follows.

TABLE 2

Treatment of *Lactobacillus plantarum* contamination

| Item | Concentration of *Lactobacillus plantarum* |
|---|---|
| Flask 1 (−bacteriophage solution) | approximately $10^8$ cfu/mL |
| Flask 2 (−bacteriophage solution) | approximately $10^9$ cfu/mL |
| Flask 1 (+bacteriophage solution) | approximately $10^1$ cfu/mL |
| Flask 2 (+bacteriophage solution) | Not detected |

From the above results, it is concluded that the bacteriophage Lac-PLP-1 of the present invention could be used as an active ingredient of the composition in order to treat the contaminations of *Lactobacillus plantarum*.

Example 6: Application Tests

The bacteriophage Lac-PLP-1 was investigated practically in the process for producing bio-ethanol whether it could be applied to improve the productive yield of bio-ethanol or not. For this application, the bacteriophage Lac-PLP-1 suspension prepared by the same manner as described in Example 1 was utilized. The application tests were performed by adding bacteriophage suspension to a yeast cream to be the bacteriophage concentration of $1 \times 10^7$ pfu/mL (test ①), putting bacteriophage suspension into a fermentation tank to be the bacteriophage concentration of $1 \times 10^6$ pfu/mL (test ②), putting bacteriophage suspension into a fermentation tank to be the bacteriophage concentration of $1 \times 10^6$ pfu/mL along with the bacteriophage suspension added to a yeast cream to be the bacteriophage concentration of $1 \times 10^7$ pfu/mL (test ③), and without any treatment (test ④). Test ④ was included as a control group. These application tests were conducted total 10 times and the results are as follows. In Table 3, the bio-ethanol productivity is average values obtained after measuring 10 times and considering that of test ④ as 100%.

TABLE 3

Results of application tests

| Item | Productivity of bio-ethanol |
|---|---|
| Test ① | 104% |
| Test ② | 106% |
| Test ③ | 108% |
| Test ④ | 100% |

From the above results, it is confirmed that the composition of the present invention comprising the bacteriophage Lac-PLP-1 could be effective to improve the productive yield of bio-ethanol.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating contaminations of *Lactobacillus plantarum*, the method comprising a step of adding a composition comprising Siphoviridae bacteriophage Lac-PLP-1 that is isolated from nature and can kill *Lactobacillus plantarum* cells specifically, which has the genome represented by the nucleotide sequence of SEQ ID NO: 1, as an active ingredient.

2. The method according to claim 1, wherein said composition is added to treat the contaminations of *Lactobacillus plantarum* in a process for producing bio-ethanol.

* * * * *